US008394418B2

(12) United States Patent
Young

(10) Patent No.: US 8,394,418 B2
(45) Date of Patent: Mar. 12, 2013

(54) COMBINATION PREPARATION OF A BIOLOGICAL RESPONSE MODIFIER AND AN ANTICANCER AGENT AND USES THEREOF

(75) Inventor: Aiping Young, North York (CA)

(73) Assignee: Erin Mills Biotech Inc., Concord, Ontario (CA)

( * ) Notice: Subject to any disclaimer, the term of this patent is extended or adjusted under 35 U.S.C. 154(b) by 87 days.

(21) Appl. No.: 13/008,304

(22) Filed: Jan. 18, 2011

(65) Prior Publication Data

US 2011/0111047 A1    May 12, 2011

Related U.S. Application Data

(63) Continuation of application No. 12/061,274, filed on Apr. 2, 2008, now abandoned, which is a continuation of application No. 11/247,026, filed on Oct. 11, 2005, now abandoned, which is a continuation of application No. 10/416,259, filed as application No. PCT/CA01/01558 on Nov. 8, 2001, now abandoned.

(30) Foreign Application Priority Data

Nov. 8, 2000    (CA) ...................... 2325361

(51) Int. Cl.
*A61K 35/413* (2006.01)
*C07D 305/14* (2006.01)
*C07D 493/00* (2006.01)

(52) U.S. Cl. .................. 424/528; 514/449; 549/510

(58) Field of Classification Search .................. 424/528; 514/449; 549/510
See application file for complete search history.

(56) References Cited

U.S. PATENT DOCUMENTS

| | | | |
|---|---|---|---|
| 4,957,910 | A | 9/1990 | Sutton et al. |
| 6,103,698 | A | 8/2000 | Barlozzari et al. |
| 6,280,774 | B1 | 8/2001 | Rang |
| 6,440,726 | B1 | 8/2002 | Resnick |
| 2003/0096950 | A1 | 5/2003 | Tuomanen et al. |
| 2004/0101511 | A1 | 5/2004 | Young |
| 2005/0192443 | A1 | 9/2005 | Young |

FOREIGN PATENT DOCUMENTS

| | | |
|---|---|---|
| WO | WO 95/07089 | 3/1995 |
| WO | WO 96/28175 A | 9/1996 |
| WO | WO 98/52585 | 11/1998 |

OTHER PUBLICATIONS

AACR Press Release, "New Agent Shows Promise in Treatment of Pancreatic Cancer", *Annual Meeting of American Associate for Cancer Research*, Philadelphia, PA U.S.A, Apr. 13, 1999.
Barenbaum, "Synergy, additivism and antagonism in immunosuppression," Clin Exp Immunol, 28:1-18, 1977.

(Continued)

*Primary Examiner* — Rosanne Kosson
(74) *Attorney, Agent, or Firm* — Saliwanchik, Lloyd & Eisenschenk

(57) ABSTRACT

The present invention provides anticancer biological response modifier combinations. In accordance with an aspect of the present invention, there is provided a combination comprising: (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) one or more anticancer agent(s), wherein said combination has therapeutic synergy or improves the therapeutic index in the treatment of cancer over the composition or the anticancer agent(s) alone. Another aspect of the present invention provides the use of this combination in the manufacture of a medicament or a pharmaceutical kit and in the treatment of cancer.

9 Claims, 25 Drawing Sheets

OTHER PUBLICATIONS

Braun, D. P. et al. (Jul. 15, 1993) "Sensitivity of Tumoricidal Function in Macrophages from Different Anatomical Sites of Cancer Patients to Modulation of Arachidonic Acid Metabolism" *Cancer Research* 53(14):3362-3368.

Corbett, T.H., P. Griswold, Jr., B.J. Roberts, J.C. Peckham, F.M. Schabel, Jr. (1977) "Evaluation of Single Agents and Combinations of Chemotherapeutic Agents in Mouse Colon Carcinomas" *Cancer* 40:2660-2680.

Corbett, T.H., B.J. Roberts, M.W. Trader, W.R. Laster, Jr. D.P. Griswold, Jr., F.M. Schabel (May 1982) "Response of Transplantable Tumors of Mice to Anthracenedione Derivative Alone and in Combination with Clinically Useful Agents" *Cancer Treatment Reports* 66(5):1187-1200.

Devita, Jr., et al., "Cancer Principles & Practice of Oncology 6$^{th}$ Ed.", *Lippincott, Williams & Wilkins*, Philadelphia, 2001, pp. 292-294.

Ferdinandi, E.S. et al. (Oct. 1999) "Virulizin—a review of its antineoplastic activity" *Expert Opinion on Investigational Drugs* 8(10):1721-1735.

Imutec Pharma. Press Release, "Imutech Pharma Received Marketing Approval for Virulizin for the Treatment of Malignant Melanoma in Mexico", Oct. 21, 1997.

Imutec Pharma. Press Release, "Imutec Pharma Releases Additional Pancreatic Cancer Cancer Data", Nov. 12, 1998.

Liu, C. et al., "A Novel Immunotherapeutic Agent for Pancreatic Cancer: Results of Preclinical and Clinical Trials Using Virulizing", *Proceedings of the American Association for Cancer Research*, Mar. 1999, pp. 575, vol. 40, No. 3793.

Liu, C. et al. (2000) "Virulizin-2 gamma, Biological Response Modifier, Treatment of pancreatic cancer" *Drugs of the Future* 25(4):356-359.

Liu, C. et al. (May 2000) "Virulizin-2 gamma, a novel immunotherapeutic agent, in treatment of human pancreatic cancer xenografts" *International Journal of Oncology* 16(5):1015-1020.

Lloyd, G. et al. "Effect of bile salts and of fusidic acid on HIV-1 infection of cultured cells" *The Lancet*, 1988, 1(8600):1418-1421.

Lorus Therapeutics Inc. Press Release, "Lorus Therapeutics Announces Final Phase I/II Trial Data", Dec. 8, 1998.

Lorus Therapeutics Inc. Press Release, Lorus's Anti-Cancer Drug Virulizin, Profiled at Annual Meeting of American Associateion for Cancer Research (AACR), Apr. 13, 1999.

Merriman, R.L. et al. (1996) "Comparison of the antitumor activity of gemcitabine and ara-C in a panel of human breast, colon, lung and pancreatic xenograft models" *Investigational New Drugs* 14(3):243-247.

Office Action from U.S. Appl. No. 10/416,259, filed Nov. 8, 2001, mail date Jul. 13, 2004.

Office Action from U.S. Appl. No. 10/416,259, filed Nov. 8, 2001, mail date Dec. 13, 2004.

Office Action from U.S. Appl. No. 10/821,649, filed Apr. 8, 2004, mail date Nov. 23, 2005.

Office Action from U.S. Appl. No. 10/416,259, filed Nov. 8, 2001, mail date Apr. 12, 2005.

Schultz, R.M. et al. (1993) "Evaluation of New Anticancer Agents against the MIA PaCa-2 and PANC-1 Human Pancreatic Carcinoma Xenografts" *Oncology Research* 5(6/7):223-228.

Siziopikou, K. et al. (Sep. 1991) "Impaired Tumoricidal Function of Alveolar Macrophages from Patients with Non-Small Cell Lung Cancer" *Cancer* 68(5):1035-1044.

Smith, P.K. et al. (1985) "Measurement of Protein Using Bicinchonic Acid" *Analytical Biochemistry* 150:76-85.

Tallarida, "Drug synergism and Dose-effect Analysis," Chapman & Hall/CRC, Boca Raton, 2000, pp. 1-13.

Tamari, M. et al. (1976) "Etudes sur les Phosphonolipides de la Bile de Boeuf" *Agr. Biol. Chem.* 40(10):2057-2062 (English abstract).

Thirlwell et al. (1994) "In Vitro Evidence for the Effects of Virulizin on Cytokine Production" *Clinical and Investigative Medicine*, XX vol. s4, No. 17, p. b88.

Thirlwell, MP, B. Zee, G. Ely (Nov. 8-11, 2000) Phase I-II Trials of a Novel Biologic Agent, Virulizin-}pi≡-Rm in Cancer of the Pancreas (Nov. 2000) *Chemotherapy Foundation Symposium XVIII Innovative Cancer Therapy for Tomorrow Presented at the 23$^{rd}$ Chemotherapy Foundation Symposium*, New York, Nov. 8, 2000.

Warner, E. et al. (Feb. 1994) "Phase II Trial of Virulizin in Patients with Pancreatic Cancer" *Clinical and Investigative Medicine*, XX, 17(1):37-41.

COMBINATION PREPARATION OF A BIOLOGICAL RESPONSE MODIFIER AND AN ANTICANCER AGENT AND USES THEREOF

CROSS-REFERENCE TO RELATED APPLICATIONS

The present application is a continuation of U.S. application Ser. No. 12/061,274, filed Apr. 2, 2008; which is a continuation of U.S. application Ser. No. 11/247,026, filed Oct. 11, 2005, now abandoned; which is a continuation application of U.S. application Ser. No. 10/416,259, filed May 8, 2003, now abandoned; which is the National Stage of International Application Number PCT/CA2001/001558, filed Nov. 8, 2001, each of which is hereby incorporated by reference herein in its entirety, including any figures, tables, nucleic acid sequences, amino acid sequences, or drawings.

FIELD OF THE INVENTION

The present invention relates to anticancer biological response modifier combinations, pharmaceutical compositions comprising the same, and the use thereof in the treatment of cancer.

BACKGROUND OF THE INVENTION

There are a number of therapies directed towards the treatment of cancer, including chemotherapeutic drugs, radiation, gene therapy and antisense oligonucleotides. One drawback to current therapies is the toxicity associated with most treatments. Moreover, oftentimes large dosages must be administered over an extended period of time in order to attain therapeutic benefit. Thus, a need remains for more effective treatments.

A bile extract has been prepared that is known to be able to modify the biological response of cells of the immune system. The production and characterization of this bile-derived Biological Response Modifier (BD-BRM) has been described in International Patent Application Serial No. PCT/CA94/00494, published Feb. 16, 1995 as WO 95/07089, International Patent Application Serial No. PCT/CA96/00152, published Sep. 19, 1996 as WO 96/28175 and U.S. Pat. No. 6,280,774. The use of this immunomodulatory composition as an anti-viral has been described in International Patent Application Serial No. PCT/CA98/00494, published Nov. 26, 1998 as WO 98/52585. These applications are herein incorporated by reference in their entirety.

The BD-BRM composition is composed of small molecular weight components of less than 3000 daltons, and has one or more of the following properties:
a) is extracted from bile of animals;
b) is capable of stimulating monocytes and/or macrophages in vitro and/or in vivo;
c) is capable of modulating tumor necrosis factor production and/or release;
d) contains no measurable level of IL-1$\alpha$, IL-1$\beta$, TNF, IL-6, IL-8, IL-4, GM-CSF or IFN-$\gamma$;
e) shows no cytotoxicity to human peripheral blood mononuclear cells or lymphocytes; and
f) is not an endotoxin.

The bile-derived biologic response modifier (BD-BRM) is a composition that has been hypothesized to exert anti-tumour activity via the activation of macrophages, with subsequent enhancement of cell-mediated immune response to tumours. Its precise mechanism of action remains unknown. The cumulative results of studies with BD-BRM revealed following:
(1) BD-BRM does not directly stimulate lymphocytes to synthesize DNA or undergo blastogenesis and cell division. BD-BRM does not directly stimulate the development of lymphocyte-mediated cytotoxicity.
(2) BD-BRM can stimulate normal peripheral blood monocytes to express cytocidal activity in a dose-dependent manner. The activity elicited by BD-BRM is equal to or greater than the activity produced in response to more conventional macrophage activators that are currently under investigation in cancer patients including: Gamma Interferon; Granulocyte-Monocyte Colony Stimulating Factor; Monocyte Colony Stimulating Factor; and Interleukin-12.
(3) BD-BRM can stimulate both the peripheral blood monocytes and regional, tumour-associated macrophages from cancer patients to express significant cytocidal activity. This included peritoneal macrophages from women with gynaecological malignancies and alveolar macrophages from patients with lung cancer. BD-BRM has been found to stimulate macrophages from cancer patients to kill autologous and heterologous tumour cells obtained from surgical specimens of patients. Of potentially greater importance is the finding that BD-BRM can often stimulate cancer patient macrophages that are unresponsive to stimulation with conventional activators such as gamma interferon+endotoxin.
(4) The hypersecretion of prostaglandins, both by macrophages and by tumor cells from cancer patients has been shown to be a principal cause of the immunosuppression seen in patients with advanced malignant disease. One determinant of the biological activity of different macrophage activators in cancer patients PBMs, therefore, is the sensitivity of the activator to arachidonic acid metabolism and the secretion by the cell of prostaglandins. The development of macrophage cytocidal function in response to BD-BRM was found to be insensitive to the inhibitory effects of prostaglandins. This is considered important therapeutically because the effectiveness of many other biological activators is limited by prostaglandins.
(5) BD-BRM can stimulate cytocidal function in macrophages obtained from cancer patients (including pancreatic cancer) who are undergoing cytotoxic therapy. Of note is the fact that BD-BRM was more effective in stimulating tumoricidal function than conventional activators such as gamma interferon plus endotoxin.
(6) BD-BRM can also stimulate cytocidal function in macrophages obtained from patients with Kaposi's sarcoma even at very late stages of the disease. Thus, the action of BD-BRM appears to be independent of the need for collaboration with other immune cell types including helper T-lymphocytes.
(7) The macrophage cytocidal function that develops in response to BD-BRM may be associated with the expression of TNF$\alpha$ by the macrophages. However, other mechanisms for cytotoxicity may also be involved. The BD-BRM composition from bovine sources promotes the release of TNF from human peripheral blood mononuclear cells and from the pre-monocyte cell line U-937 in what appears to be physiological quantities. Because TNF is known to initiate a cascade of inflammatory and antitumor cytokine effects, the composition could exert its antineoplastic effect by stimulating human leukocytes to release TNF (and possibly other cytokines).
(8) Demonstrates anti-tumour activity in a mouse tumour (plasmacytoma) model.

(9) Exhibits no toxicity in animals at doses up to 125× the doses used in human toxicity studies with no $LD^{50}$ yet reached in toxicity studies.
(10) Induces the phenomenon of apoptosis in some continuous cell lines.
(11) Is non-cytotoxic to human PBMNs and lymphocytes. The survival of human peripheral blood mononuclear cells (PBMNs) and lymphocytes is not affected by BD-BRM.

The central hypothesis guiding investigations of the BD-BRM composition is that the therapeutic efficacy of a powerful biological stimulator can depend on its ability to elicit suitable modulation of the immune system, such as by activating macrophages and/or monocytes to produce certain cytokines or promote activity to seek and remove or destroy disease-causing viruses or cells negatively affected by such viral infections. Such function could be generated by direct stimulation of resident immune cells in tumour microenvironments. Alternatively, this function could be generated by stimulation of circulating immune cells if those cells were then able to home in on tumour sites and to function in that environment.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are hereby incorporated by reference in their entireties in this application.

SUMMARY OF THE INVENTION

An object of the present invention is to provide anticancer biological response modifier combinations. In accordance with an aspect of the present invention, there is provided a combination comprising: (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) one or more anticancer agent(s), wherein said combination has therapeutic synergy or improves the therapeutic index in the treatment of cancer over the composition or the anticancer agent(s) alone. Another aspect of the present invention provides the use of this combination in the manufacture of a medicament or a pharmaceutical kit.

In accordance with another aspect of the invention, there is provided a pharmaceutical kit comprising: (i) a dosage unit of a composition and a pharmaceutically acceptable carrier wherein the composition comprises small molecular weight components of less than 3000 daltons, and has the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) a dosage unit of one or more chemotherapeutic drug(s) and a pharmaceutically acceptable carrier, (i) and (ii) being provided in amounts that are effective, in combination, for killing tumour or metastatic cells.

In accordance with another aspect of the invention, there is provided a pharmaceutical composition comprising: (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; (ii) one or more chemotherapeutic drug(s); and (iii) a pharmaceutically acceptable carrier; wherein said pharmaceutical composition has therapeutic synergy or improves the therapeutic index in the treatment of cancer over the composition or the chemotherapeutic drug(s) alone.

In accordance with another aspect of the invention, there is provided a combination for use in the treatment of cancer, comprising: (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) one or more anticancer agent(s), wherein said combination has therapeutic synergy or improves the therapeutic index in the treatment of cancer over the composition or the anticancer agent(s) alone.

In accordance with another aspect of the invention, there is provided a method for treating cancer, comprising the step of administering a therapeutically effective amount of a combination comprising: (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) one or more anticancer agent(s), wherein said combination has therapeutic synergy or improves the therapeutic index in the treatment of cancer over the composition or the anticancer agent(s) alone.

BRIEF DESCRIPTION OF THE DRAWINGS

Further details of the invention are described below with the help of the examples illustrated in the accompanying drawings in which.

DETAILED DESCRIPTION OF THE INVENTION

Figure 1:
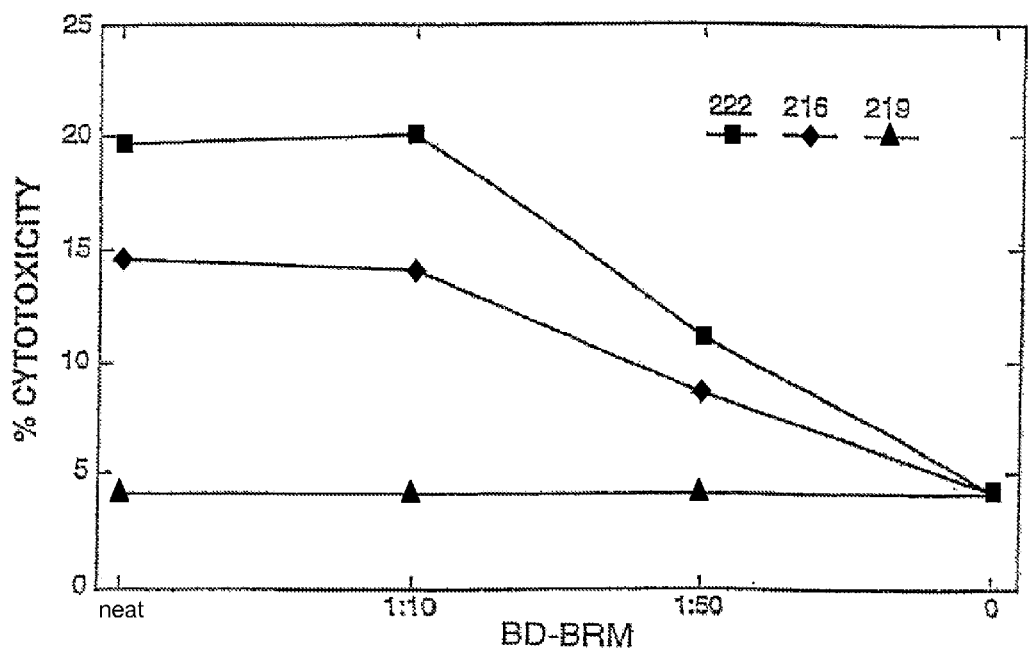
FIG. 1 is a graph showing dose response of the composition of the invention in stimulating peripheral blood monocyte function.

The present invention provides anticancer biological response modifier (BD-BRM) combinations. The combination comprises (i) a composition comprising small molecular weight components of less than 3000 daltons, and having the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) one or more anticancer agent(s), wherein the BD-BRM combination has therapeutic synergy or improves the therapeutic index in the treatment of cancer over the composition or the anticancer agent(s) alone. The present invention further provides the use of the combination in the manufacture of a medicament or a pharmaceutical kit and in the treatment of cancer.

Components of the Combination
BD-BRM Composition

Experimental evidence to date indicates that the unique immunomodulatory properties of BD-BRM activity are associated with low molecular weight material derived from bile. The BD-BRM composition of the present invention comprises small molecular weight components of less than 3000 daltons, and having at least one of the following properties:

a) is extracted from the bile of animals;
b) is capable of stimulating or activating monocytes and/or macrophages in vitro and/or in vivo;
c) is capable of modulating tumor necrosis factor production and/or release;
d) contains no measurable level of IL-1α, IL-1β, TNF, IL-6, IL-8, IL-4, GM-CSF or IFN-γ;
e) shows no cytotoxicity to human peripheral blood mononuclear cells or lymphocytes; and
f) is not an endotoxin.

As mentioned above, the production and characterization of the BD-BRM composition has been described in preceding patent applications, and is also summarized in Example 1. The composition can be produced in a consistently reproducible form using the method as generally described above with demonstrated identity, potency and purity from batch to batch. Identity and purity are determined using reverse-phase high pressure liquid chromatography. (See Example 1). The compositions have a consistently reproducible pattern on reverse-phase HPLC. The composition may be used in a concentrated form. The composition may also be lyophilized. The composition may be used without further modification by simply packaging it in vials and sterilizing.

The compositions are also characterized by the properties hereinbefore mentioned, for example their ability to stimulate monocytes and macrophages in vitro and in vivo, etc. The compositions activate PBMNs to release TNF in vitro as measured by the Monocyte/Macrophage Activation Assay (TNF-Release).

Anticancer Agents

This invention provides for a BD-BRM composition in combination with one or more other anticancer agents. An "anticancer agent" is any compound, composition or treatment that prevents or delays the growth and/or metastasis of cancer cells. Such anticancer agents include but are not limited to chemotherapeutic drug treatment, radiation, gene therapy, hormonal manipulation, immunotherapy and antisense oligonucleotide therapy. It is to be understood that anticancer agents for use in the this invention also include novel compounds or treatments developed in the future that can be used to generate therapeutic combinations as described herein.

Examples of candidate anti-cancer compounds that may be useful in the combinations of this invention are: antisense sequences, Drugs for Promyelocytic Leukemia: Tretinoin (Vesanoid®); Drugs for Chronic Myeloid Leukemia: Low-dose Interferon (IFN)-alpha; Drugs Used in Gastric Cancer: Antibiotics, Antineoplastics; Acute Lymphoblastic Leukemia: Pegaspargase (Oncaspar®), Rhone-poulenc Rorer, L-asparaginase, 11-2; Drugs for Colon Cancer: Edatrexate or 10-ethyl-10-deaza-aminopterin or 10-edam, 5-fluorouracil (5-FU) and Levamisole, Methyl-ccnu (Methyl-chloroethyl-cyclohexyl-nitrosourea). Fluorodeoxyuridine (Fudr), Vincristine; Drugs for Esophageal Cancer: Porfimer Sodium (Photofrin®), Quadra Logic Technologies, or Treatment with a Neodymium:yag (Nd:yag®) Laser; Drugs Used in Colorectal Cancer: Irinotecan (Camptosar®), Pharmacia & Upjohn, Topotecan (Hycamtin®), Loperamide (Imodium®), 5-fluorouracil (5-FU); Drugs For Advanced Head and Neck Cancers: Docetaxel (Taxotere®); Drugs for Non-hodgkin's Lymphoma: Rituximab, Etoposide; Drugs for Non-small-cell Lung Cancer: A Vinca Alkaloid, Vinorelbine Tartrate (Navelbine®), Wellcome, Paitaxel, (Taxol®), Docetaxel (Taxotere®), Topotecan, Irinotecan, Gemcitabine; Drugs for Ovarian Cancer: Docetaxel (Taxotere®), Gemcitabine, (Gemzar®), Irinotecan (Camptosar®), Paclitaxel (Taxol®), Topotecan (Hycamtin®), Amifostine (Ethyol®), Us Bioscience (For Reducing the Cumulative Renal Toxicity Associated with Repeated Cisplatin Therapy in Patients with Advanced Ovarian Cancer); Drugs to Prevent Melanoma (Sun Screens): 2-ethylhexyl-p-methoxy-cinnamate (2-ehmc), Octyl-N-dimethyl-p-aminobenzoate (O-paba), Benzophenone-3 (Bp-3); Drugs for Prostate Cancer Flutamide (Eulexin®), Finasteride (Proscar®), Terazosin (Hytrin®), Doxazosin (Cardura®), Goserelin Acetate (Zoladex®), Liarozole, Nilutamide (Nilandron®), Mitoxantrone (Novantrone®), Prednisone (Deltasone®); Drugs for Pancreatic Cancer: Gemcitabine (Gemzar®), 5-fluorouracil; Drugs for Advanced Renal Cancer: Interleukin-2 (Proleukin®), Chiron Corp.; Additional Anti-neoplastic Drugs: Porfimer Sodium, Axcan, Dacarbazine, Faulding, Etoposide, Faulding, Procarbazine HCl, Sigma-tau, Rituximab, Roche, Paclitaxel (Taxol®), Bristol-myers Squibb, Trastuzumab (Herceptin®), Roche, Temozolomide (Temodal®), Schering; Alkylating Agents Used in Combination Therapy for Different Cancers: Cyclophosphamide, Cisplatin, Melphalan.

Antisense Compounds

The specificity and sensitivity of antisense compounds makes them useful in diagnostics, therapeutics, prophylaxis, as research reagents and in kits. In the context of the present invention, the terms "antisense compound" and "antisense oligonucleotide" each refer to an oligomer or polymer of ribonucleic acid (RNA), or deoxyribonucleic acid (DNA), or mimetics thereof. These terms also include chimeric antisense compounds, which are antisense compounds that contain two or more chemically distinct regions, each made up of at least one monomer unit. In accordance with the present invention, the terms "antisense compound" and "antisense oligonucleotide" further include oligonucleotides composed of naturally occurring nucleobases, sugars and covalent internucleoside (backbone) linkages, as well as oligonucleotides comprising non-naturally-occurring moieties that function similarly. Such modified or substituted oligonucleotides are well known to workers skilled in the art and often preferred over native forms because of desirable properties such as, for example, enhanced cellular uptake, enhanced affinity for nucleic acid target and increased stability in the presence of nucleases. The antisense compounds in accordance with the present invention comprise from about 7 to about 50 nucleobases, or from about 7 to about 30. Alternatively, the antisense compounds comprise a mixture of short oligomers which will bind to the target nucleic acid in tandem (i.e. they are complementary to sequences that are adjacent to one another in the target nucleic acid).

Examples of antisense compounds useful in the present invention include oligonucleotides containing modified backbones or non-natural internucleoside linkages. In accordance with the present invention, oligonucleotides having modified backbones include those that retain a phosphorus atom in the backbone and those that do not have a phosphorus atom in the backbone. For the purposes of the present invention, and as sometimes referenced in the art, modified oligonucleotides that do not have a phosphorus atom in their internucleoside backbone can also be considered to be oligonucleosides.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may be additionally or alternatively employed. Similar techniques using phosphorothioates and alkylated derivatives have been employed to produce oligonucleotides.

Antisense oligonucleotides have been successfully employed as therapeutic moieties in the treatment of disease states such as cancer. Antisense compounds exert their effects by specifically modulating expression of a gene implicated in a specific disease state. Thus, the present invention contemplates the therapeutic administration of an effective amount of a combination of the BD-BRM composition of the present invention and an appropriate antisense compound to a mammal suspected of having a disease or disorder which can be treated by specifically modulating gene expression. The present invention further contemplates the prophylactic use of a combination of the BD-BRM composition and an antisense compound in the prevention of a cancer which is related to over- or under-expression of a specific gene.

Pharmaceutical Compositions

The combinations of the present invention may be converted using customary methods into pharmaceutical compositions. The pharmaceutical composition contain the combination of the invention either alone or together with other active or inactive substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, gels, membranes, and tubelets. For parenteral and intracerebral uses, those forms for intramuscular or subcutaneous administration can be used, or forms for infusion or intravenous or intracerebral injection can be used, and can therefore be prepared as solutions of the combinations or as powders of the combinations to be mixed with one or more pharmaceutically acceptable excipients or diluents, suitable for the aforesaid uses and with an osmolarity that is compatible with the physiological fluids. For local use, those preparations in the form of creams or ointments for topical use or in the form of sprays may be considered; for inhalant uses, preparations in the form of sprays, for example nose sprays, may be considered. Preferably, the BD-BRM composition of the combination is administered intramuscularly.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in *Remington's Pharmaceutical Sciences* (Nack Publishing Company, Easton, Pa., USA 1985).

On this basis, the pharmaceutical compositions include, albeit not exclusively, the combination of the invention in association with one or more pharmaceutically acceptable vehicles or diluents, and are contained in buffered solutions with a suitable pH and iso-osmotic with the physiological fluids.

The compositions and agents of the invention are intended for administration to humans or animals.

The dosage requirements of the pharmaceutical compositions according to the present invention will vary with the particular combinations employed, the route of administration and the particular cancer and cancer patient being treated. Treatment will generally be initiated with small dosages less than the optimum dose of the compound. Thereafter the dosage is increased until the optimum effect under the circumstances is reached. In general, the pharmaceutical compositions according to the present invention are most administered at a concentration that will generally afford effective results without causing any harmful or deleterious side effects. The compounds can be administered either as a single unit dose, or if desired, the dosage can be divided into convenient subunits administered at suitable times throughout the day. The amount of the pharmaceutical composition that will be effective in treatment can be determined by standard clinical techniques, known to a worker skilled in the art

[for example, see *Remington's Pharmaceutical Sciences*, 18th Edition, Mack Publishing Co., Easton, Pa. (1990)].

Therapeutic Activity of the Combination

The combination of the present invention has a net anticancer effect that is greater than the anticancer effect of the individual components of the combination when administered alone. The anticancer effect is increased without a concomitant increased toxic effect. Without being limited by mechanism, by combining one or more anticancer agents with a BD-BRM composition it is possible to:
(i) increase the therapeutic effect of the anticancer agent(s);
(ii) increase the therapeutic effect of the BD-BRM composition;
(iii) decrease or delay the toxicity phenomena associated with the anticancer agent(s); and/or
(vi) decrease or delay the toxicity phenomena associated with the BD-BRM composition, in comparison to treatment with the individual components of the combination.

In one embodiment the combination of the present invention provides an improved efficacy, over treatment using the components of the combination alone, that may be demonstrated by determination of the therapeutic synergy.

A combination manifests therapeutic synergy if it is therapeutically superior to one or other of the constituents used at its optimum dose [T. H. Corbett et al., (1982) *Cancer Treatment Reports*, 66, 1187]. To demonstrate the efficacy of a combination, it may be necessary to compare the maximum tolerated dose of the combination with the maximum tolerated dose of each of the separate constituents in the study in question. This efficacy may be quantified using techniques and equations commonly known to workers skilled in the art. [T. H. Corbett et al., (1977) *Cancer*, 40, 2660.2680; F. M. Schabel et al., (1979) Cancer Drug Development, Part B, Methods in Cancer Research, 17, 3-51, New York, Academic Press Inc.].

The combination, used at its own maximum tolerated dose, in which each of the constituents will be present at a dose generally not exceeding its maximum tolerated dose, will manifest therapeutic synergy when the efficacy of the combination is greater than the efficacy of the best constituent when it is administered alone.

In another embodiment the combination of the present invention improves the therapeutic index in the treatment of cancer over that of the BD-BRM composition or the anticancer agent(s) when administered to a patient alone.

A median effective dose ($ED_{50}$) of a drug is the dose required to produce a specified effect in 50% of the population. Similarly, the median lethal dose ($LD_{50}$) of a drug, as determined in preclinical studies, is the dose that has a lethal effect on 50% of experimental animals. The ratio of the $LD_{50}$ to the $ED_{50}$ can be used as an indication of the therapeutic index. Alternatively the therapeutic index can be determined based on doses that produce a therapeutic effect and doses that produce a toxic effect (e.g. $ED_{90}$ and $LD_{10}$, respectively). During clinical studies, the dose, or the concentration (e.g. solution, blood, serum, plasma), of a drug required to produce toxic effects can be compared to the concentration required for the therapeutic effects in the population to evaluate the clinical therapeutic index. Methods of clinical studies to evaluate the clinical therapeutic index are well known to workers skilled in the art.

In one embodiment the combination of the present invention provides an improved therapeutic index, in comparison to that of the individual components of the combination when administered alone, by decreasing the observed $LD_{50}$ of at least one of the one or more anticancer agents in the combination.

In a related embodiment the combination of the present invention provides an improved therapeutic index, in comparison to that of the individual components of the combination when administered alone, by increasing the observed $ED_{50}$ of at least one of the one or more anticancer agents in the combination. In a further embodiment the combination of the present invention provides an improved therapeutic index, in comparison to that of the individual components of the combination when administered alone, by increasing the observed $ED_{50}$ of the bile-derived biological response modifier.

In another embodiment the efficacy of a combination according to the present invention may also be characterized by adding the actions of each constituent.

In order to prepare a combination according to the present invention one first selects one or more candidate anticancer agent(s) and measure its efficacy in a model of a cancer of interest, as would be well understood by one skilled in the art. The next step may be to perform a routine analysis to compare the efficacy of the one or more anticancer agent(s) alone to the efficacy of the one or more anticancer agent(s) in combination with varying amounts of the BD-BRM composition. Successful candidates for use in the combinations of the present invention will be those that demonstrate a therapeutic synergy with the BD-BRM or that improve the therapeutic index in comparison to the therapeutic index of the candidate agent(s).

The efficacy of the combinations of the present invention may be determined experimentally using standard techniques using cancer models well known to workers skilled in the art. Such cancer models allow the activity of combinations to be tested in vitro and in vivo in relation to the cancer of interest. Exemplary methods of testing activity are described in the Examples provided herein, although, it should be understood that these methods are not intended to limit the present invention.

One example of a method for studying the efficacy of the combinations on solid tumors in vivo involves the use of subject animals, generally mice, that are subcutaneously grafted bilaterally with 30 to 60 mg of a tumor fragment on day 0. The animals bearing tumors are mixed before being subjected to the various treatments and controls. In the case of treatment of advanced tumors, tumors are allowed to develop to the desired size, animals having insufficiently developed tumors being eliminated. The selected animals are distributed at random to undergo the treatments and controls. Animals not bearing tumors may also be subjected to the same treatments as the tumor-bearing animals in order to be able to dissociate the toxic effect from the specific effect on the tumor. Chemotherapy generally begins from 3 to 22 days after grafting, depending on the type of tumor, and the animals are observed every day. The different animal groups are weighed 3 or 4 times a week until the maximum weight loss is attained, and the groups are then weighed at least once a week until the end of the trial.

The tumors are measured 2 or 3 times a week until the tumor reaches approximately 2 g, or until the animal dies if this occurs before the tumor reaches 2 g. The animals are autopsied when sacrificed. The antitumour activity is determined in accordance with various recorded parameters.

For a study of the combinations on leukaemias, the animals are grafted with a particular number of cells, and the antitumour activity is determined by the increase in the survival time of the treated mice relative to the controls.

Administration of the Combination

The uses and methods of the present invention comprise administering to a subject in need thereof an effective amount of a BD-BRM composition in combination with one or more anticancer agents to a subject. As used herein, combination components are said to be administered in combination when the two or more components are administered simultaneously or are administered independently in a fashion such that the components will act at the same time.

Components administered independently can, for example, be administered separately (in time) or concurrently. Separately in time means at least minutes apart, and potentially hours, days or weeks apart. The period of time elapsing between the administration of the components of the combination of the invention can be determined by a worker of skill in the art, and will be dependent upon, for example, the age, health, and weight of the recipient, nature of the combination treatment, side effects associated with the administration of other component(s) of the combination, frequency of administration(s), and the nature of the effect desired. Components of the combinations of the invention may also be administered independently with respect to location and, where applicable, route of administration.

In another embodiment, an effective amount of a therapeutic composition comprising a BD-BRM composition and one or more anticancer agents, and a pharmaceutically acceptable carrier is administered to a subject. The combination or the pharmaceutical composition of the invention can be administered before during or after other anticancer treatment(s), or treatments for other diseases or conditions. For example a drug to treat adverse side effects of the anticancer treatment(s) can be administered concurrently with a combination of the invention or a pharmaceutical composition of the invention.

As indicated above the components of the combination of the present invention may be administered separately, concurrently, or simultaneously. In the case of separate administration the BD-BRM composition may be administered before, during or after administration of the anticancer agent(s). Furthermore, it would be readily apparent to a worker skilled in the art that the route of administration of each component of the combination is selected in order to maximize the therapeutic benefit of the component and it is not necessary that each component be delivered via the same route. The BD-BRM composition and/or the anticancer agent(s) of the combination may be administered via a single dose or via continuous perfusion.

The agents, compounds and compositions of this invention can be utilised in vivo, ordinarily in mammals, such as humans, sheep, horses, cattle, pigs, dogs, cats, rats and mice, or in vitro to treat cancer or cancer cells.

Cancers

As used herein, "cancer" refers to all types of cancer or neoplasm or malignant tumors found in mammals, including carcinomas and sarcomas. Examples of cancers are cancer of the brain, breast, cervix, colon, head and neck, kidney, lung, non-small cell lung, melanoma, mesothelioma, ovary, sarcoma, stomach, uterus and Medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, homoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas include chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Pharmaceutical Kits

The present invention additionally provides for therapeutic kits containing (i) a dosage unit of a composition and a pharmaceutically acceptable carrier wherein the composition comprises small molecular weight components of less than 3000 daltons, and has the following properties: is extracted from bile of animals; is capable of stimulating monocytes and/or macrophages in vitro and/or in vivo; is capable of modulating tumor necrosis factor production and/or release; contains no measurable level of IL-1α, IL-1β, TNF, IL-6, IL-8, IL-4, GM-CSF or IFN-gamma; is not cytotoxic to human peripheral blood mononuclear cells; is not an endotoxin; and (ii) dosage unit of one or more chemotherapeutic drug(s) and a pharmaceutically acceptable carrier, said (i) and (ii) being provided in amounts that are effective, in combination, for selectively killing tumor or metastatic cells.

As used herein, a "dosage unit" is a pharmaceutical composition or formulation comprising at least one active ingredient and optionally one or more inactive ingredient(s). The dosage unit can be unitary, such as a single pill or liquid, containing all of the desired active ingredients and the inactive ingredients necessary and desired for making a dosage suitable for administration (e.g., tabletting compounds such as binders, fillers, and the like); the dosage unit can consist of a number of different dosage forms (e.g., pill(s) and/or liquid(s)) designed to be taken simultaneously as a dosage unit.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

EXAMPLES

A worker skilled in the art can produce BD-BRM compositions, and assay BD-BRM compositions for activities such as in vitro and/or in vivo monocyte and/or macrophage stimulation, modulation of tumor necrosis factor production and/or release, content of IL-1α, IL-1β, TNF, IL-6, IL-8, IL-4, GM-CSF or IFN-gamma and endotoxin and cytotoxicity to human peripheral blood mononuclear cells, using the methods described in International Patent Application Serial No. PCT/CA94/00494, published Feb. 16, 1995 as WO 95/07089.

Example 1

In Vivo Evaluation of Efficacy of BD-BRM in the Treatment of Human Pancreatic Adenocarcinoma in CD-1 Nude Mice The mouse xenograft model of neoplasia was used in these studies to demonstrate the effect of treatment with a BD-BRM composition on tumor growth in mice. For comparison, separate groups of mice were treated with saline (control), a conventional chemotherapeutic drug or concurrently with a combination of a BD-BRM composition and a chemotherapeutic drug.

A human carcinoma cell line was grown as monolayer culture in Minimum essential medium (α-MEM) supplemented with 10% fetal bovine serum (FBS), 0.1 mM non-essential amino acid, 1.0 mM sodium pyruvate, 100 U/ml penicillin, 100 µg/ml streptomycin and 0.25 µg/ml amphotericin B and 2 mM L-alanyl-1-glutamine at 37° C. in an atmosphere of 5% $CO_2$ in air. The tumor cells were routinely subcultured twice weekly by trypsin-EDTA treatment. The cells were harvested from subconfluent logarithmically growing culture by treatment with trypsin-EDTA and counted for tumor inoculation. The cell lines used in the experiments herein are listed hereafter, though any carcinoma cell line capable of tumor formation upon inoculation could be used:

pancreatic adenocarcinoma (BxPC-3) (a gemcitabine-resistant cell line)

melanoma (A2058)

melanoma (C8161)

breast adenocarcinoma (MDA-MB-231)

prostate carcinoma (PC-3)

ovary adenocarcinoma (SK-OV-3)

large cell lung adenocarcinoma (H460)

small cell lung carcinoma (H209).

Tumor Inoculation: An acclimation period of at least 7 days was allowed between receipt of the immunocompromised animal and its inoculation. Typically CD-1 or SCID mice were used. When the female mice were 6-9 (most typically 6-7) weeks of age, each mouse was subcutaneously injected in the right flank with 3-10 million human carcinoma cells in 0.1 ml of PBS. Inoculated animals were divided into equal sized treatment groups of 9-20 (typically about 10) mice each and treated daily with saline (0.2 ml/mouse/day, i.p.), BD-BRM (0.2 ml/mouse/day, i.p.), a chemotherapeutic drug, or concurrently with BD-BRM (0.2 ml/mouse/day, i.p.) and a chemotherapeutic drug. The drug doses used in the experiments herein are listed hereafter, though any chemotherapeutic drug(s) or other anticancer agent(s) could be used:
gemcitabine (100 mg/kg in 0.1 ml saline/mouse/3 day, i.v.)
dacarbazine (DTIC) (80 mg/kg in 0.1 ml saline/mouse/day, i.p.)
taxol (10 mg/kg/week, i.v.)
5-fluorouracil
taxotere
cisplatin
mitoxanthrone (i.v.)

Tumour sizes were measured every other day in two dimensions using a caliper, and the volume was expressed in mm$^3$ using the formula: V=0.5 a×b$^2$, where a and b are the long and short diameters of the tumor, respectively. Mean tumor volumes calculated from each measurement were then plotted in a standard graph to compare the anti-tumor efficacy of drug treatments to that of control. A day after the last treatment, tumors were excised from the animals and their weights were measured. The data are displayed as a tumour growth curve, and a bar graph showing mean tumor weights.

generally begins 3 days to 4 weeks after grafting, depending on the type of tumor, and the animals are observed and animal weight change recorded, and the tumors measured regularly, for example daily, or 2 or 3 times per week until the tumor reaches a defined size (e.g. 2 g in a mouse), or until the animal dies if this occurs before the tumor reaches 2 g. The animals are autopsied when sacrificed. To study leukemia, cancerous cells can be injected intravenously. Antitumor activity is determined by the increase in the survival time of the treated animals relative to the controls. The efficacy of the treatment with the combination of the invention is assessed in terms of changes in the mean survival time of the animal. Alternative methods of assessing efficacy, and therapeutic synergy, can also be used.

These animal models are recognized in the art to be predictive tests for anticancer effects in humans.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

| Mouse xenograft experiments with BD-BRM compositions and BD-BRM combinations | | | | | | |
|---|---|---|---|---|---|---|
| Figure # | Human carcinoma | cell line | Mouse strain | drug | combination expt | # mice with total tumor regression |
| 2, 3 | pancreatic | BxPC-3 | CD-1 | gemcitabine | — | BRM: 4 (of 9) |
| 4, 5 | pancreatic | SU.86.86 | CD-1 | gemcitabine | gemcitabine | |
| 6, 7 | melanoma | A2058 | CD-1 | dacarbazine | dacarbazine | |
| 8, 9 | melanoma | C8161 | CD-1 | — | dacarbazine | comb: 5 (of 10) |
| 10, 11 | breast | MDA-MB- | CD-1 | Taxol | Taxol | |
| 12, 13 | breast | MDA-MB- | CD-1 | Taxol | Taxol | BRM: 2; comb: 5 (of |
| 14, 15 | prostate | PC-3 | SCID | mitoxantron | — | |
| 16 | pancreatic | BxPC-3 | CD-1 | 5-fluoroura | 5-fluorouraci | comb: (5 of 10) |
| 17 | pancreatic | SU.86.86 | CD-1 | 5-fluoroura | 5-fluorouraci | |
| 18, 19 | prostate | DU145 | SCID | mitoxantron | — | |
| 20 | ovarian | SK-OV-3 | CD-1 | cisplatin | cisplatin | |
| 21 | ovarian | SK-OV-3 | CD-1 | taxol | taxol | |
| 22, 23 | lung, large cell | H460 | CD-1 | taxotere | taxotere | |
| 24, 25 | lung, small cell | H209 | SCID | — | — | |

Figure 2:
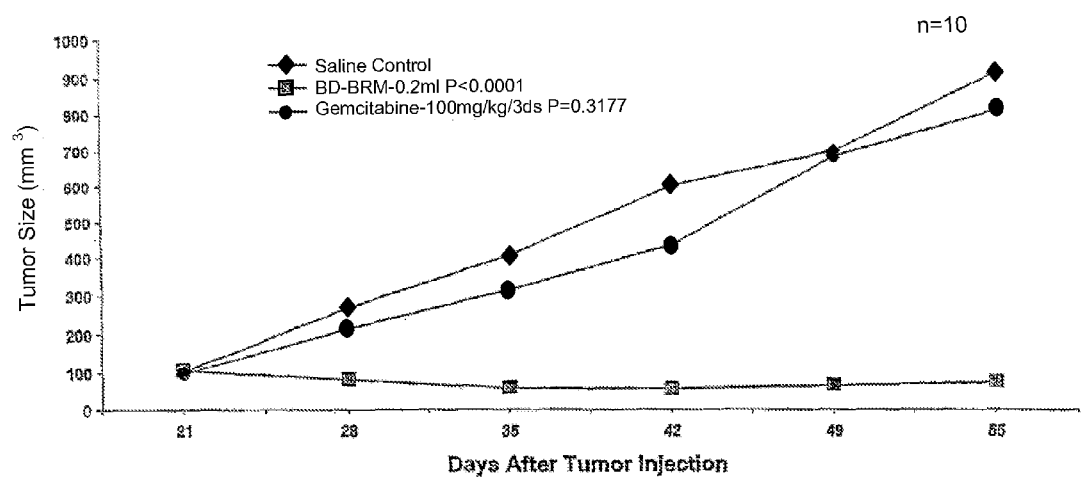
FIG. 2 illustrates the growth of Human Pancreatic Adenocarcinoma (BxPC-3) in CD-1 Nude Mice.
Figure 3:
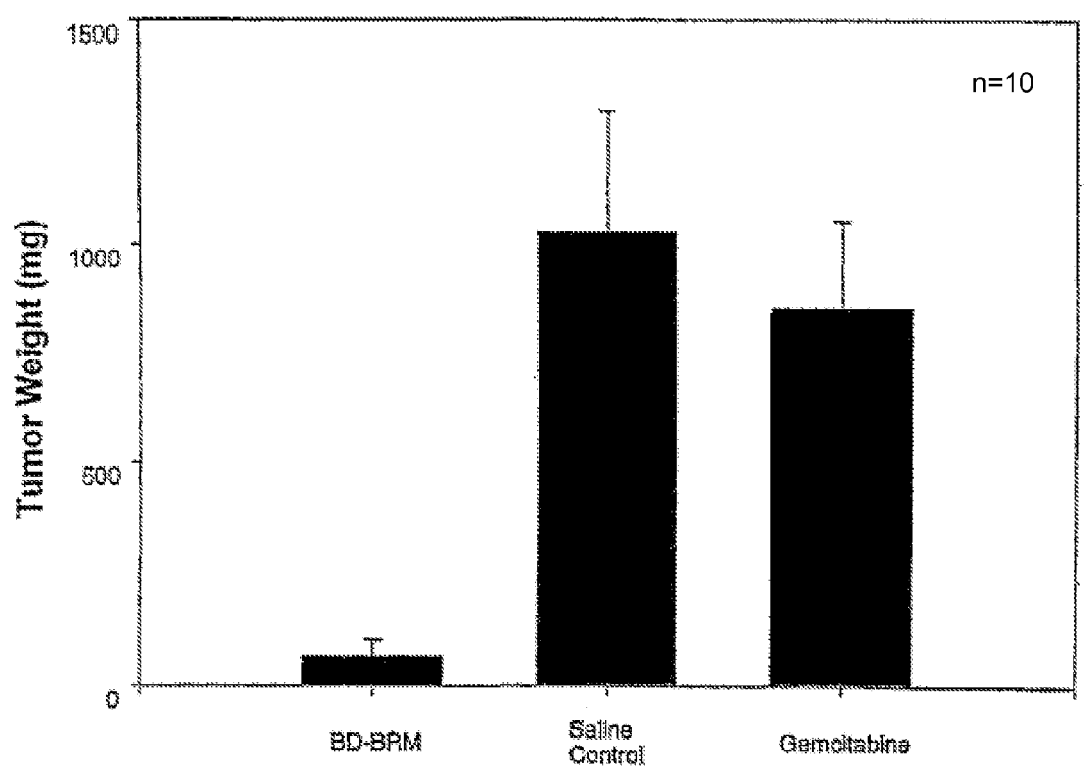
FIG. 3 illustrates the weight of Human Pancreatic Adenocarcinoma (BxPC-3) in CD-1 Nude Mice.
Figure 4:
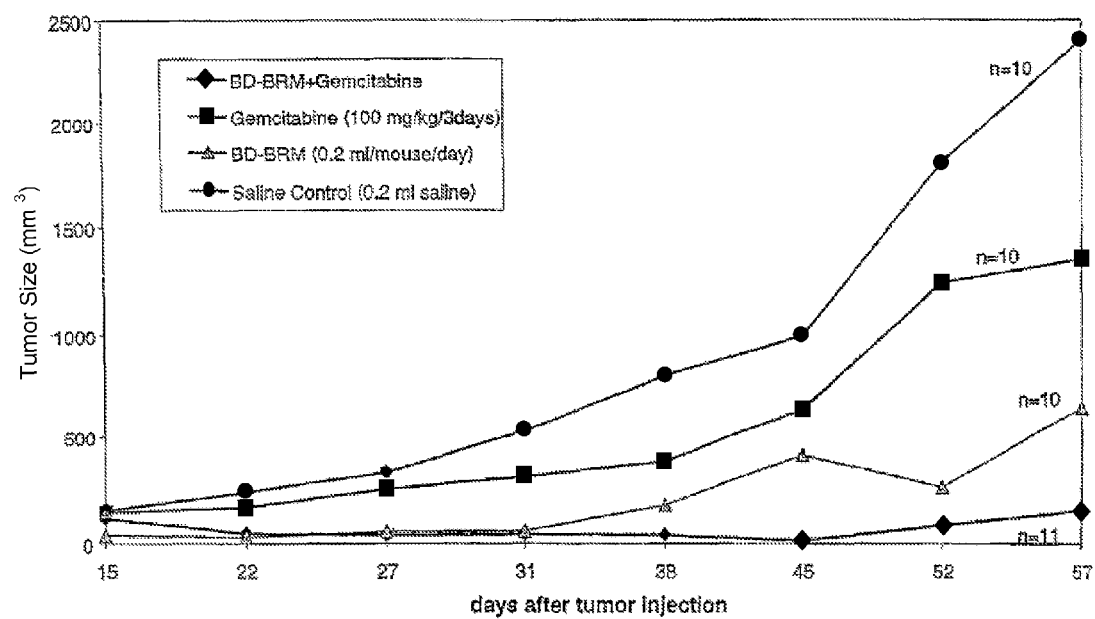
FIG. 4 illustrates the growth of Human Pancreatic Carcinoma (SU.86.86.) in CD-1 Nude Mice.
Figure 5:
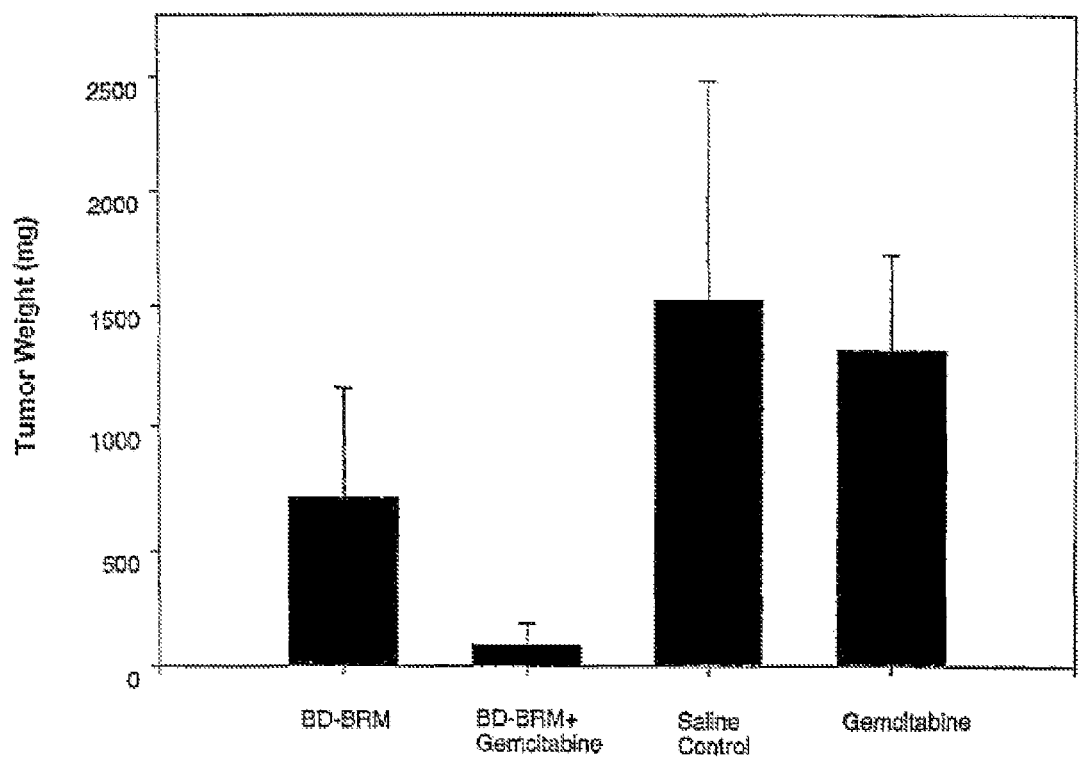
FIG. 5 illustrates the weight of Human Pancreatic Carcinoma (SU.86.86.) in CD-1 Nude Mice.
Figure 6:
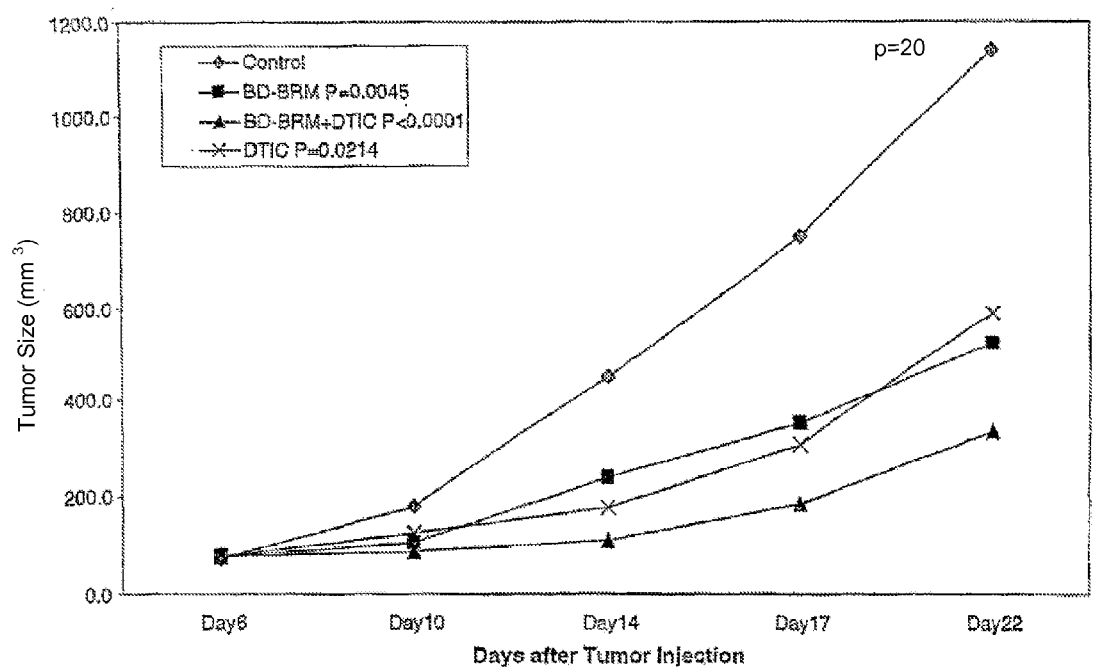
FIG. 6 illustrates the growth of Human Melanoma (A2058) in CD-1 Nude Mice.
Figure 7:
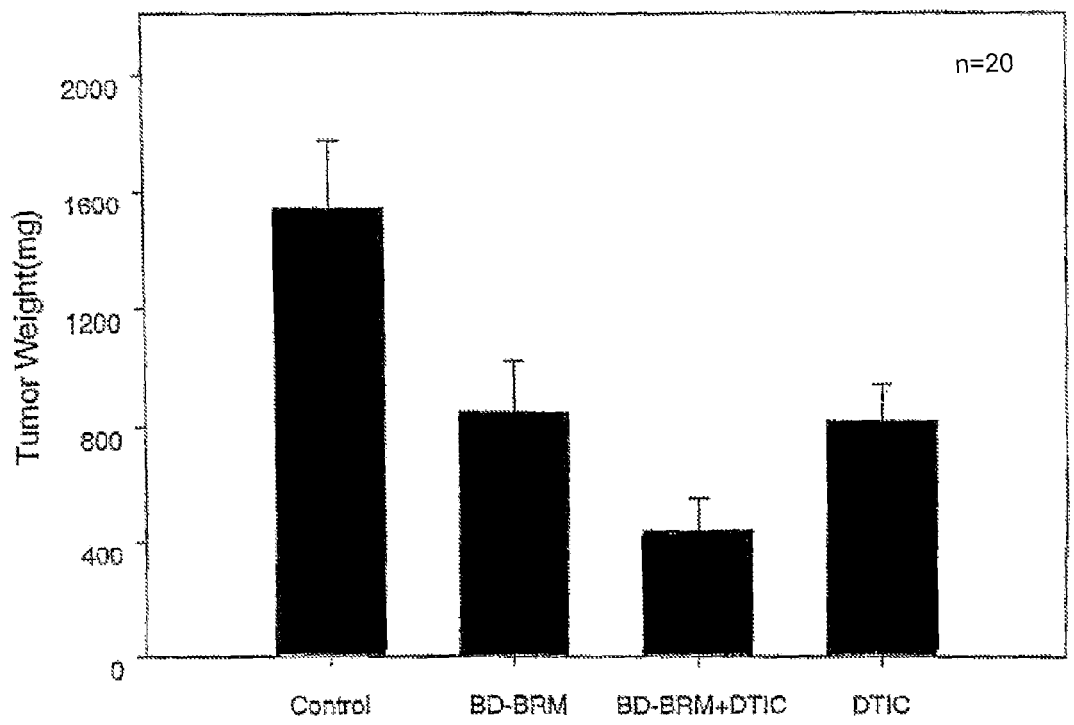
FIG. 7 illustrates the weight of Human Melanoma (A2058) in CD-1 Nude Mice.
Figure 8:
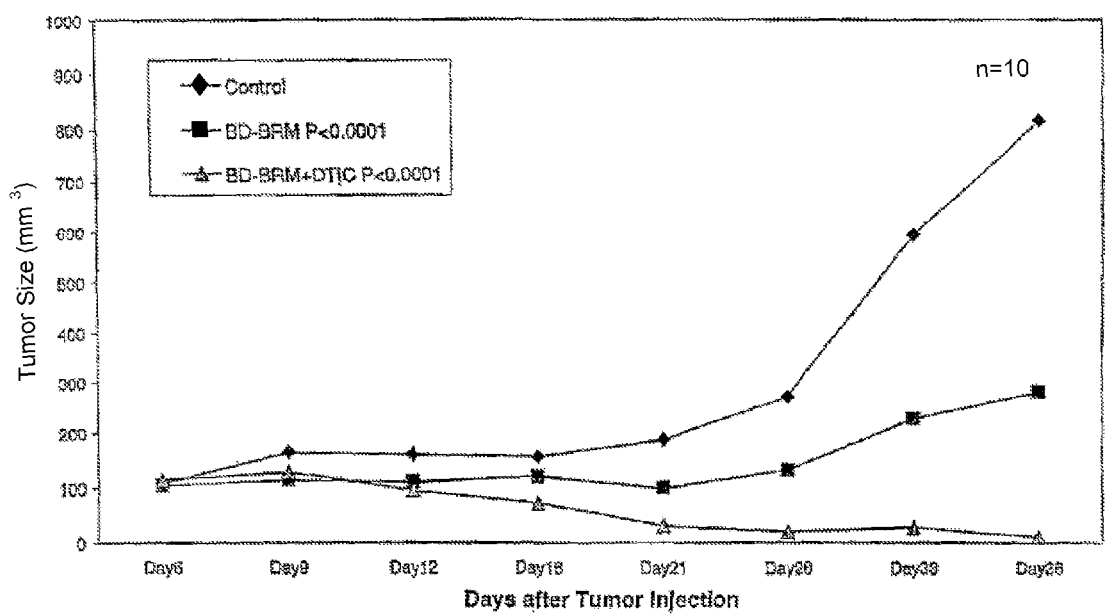
FIG. 8 illustrates the growth of Human Melanoma (C8161) in CD-1 Nude Mice.
Figure 9:
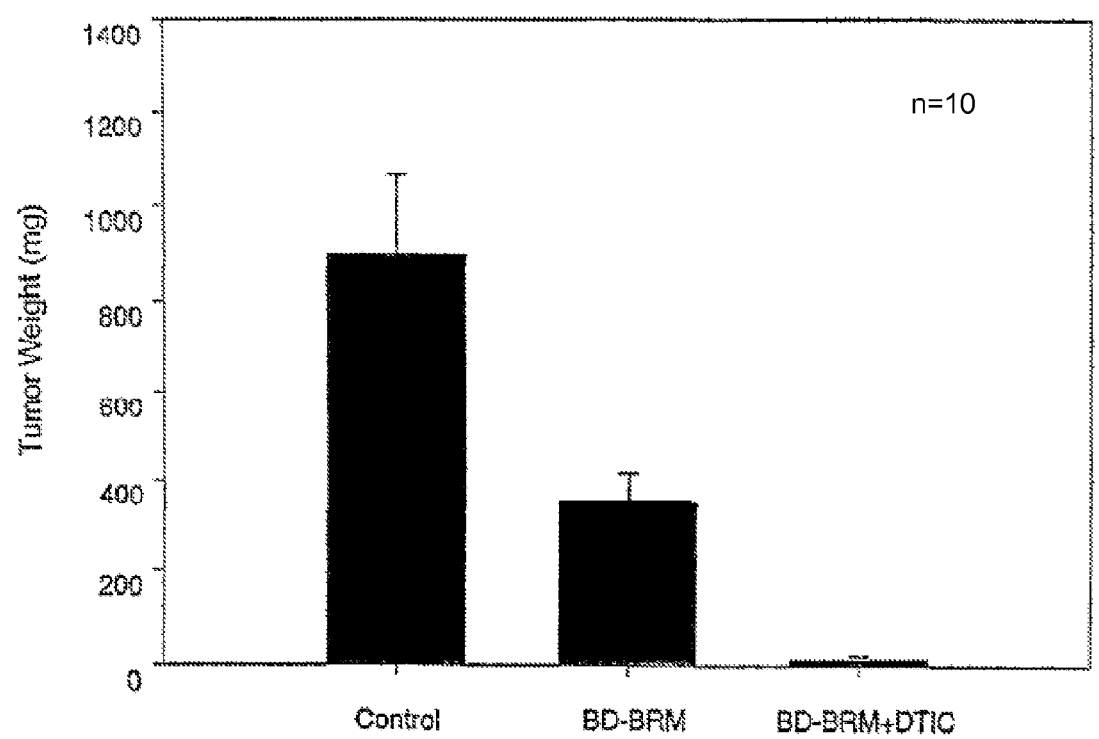
FIG. 9 illustrates the weight of Human Melanoma (C8161) in CD-1 Nude Mice.
Figure 10:
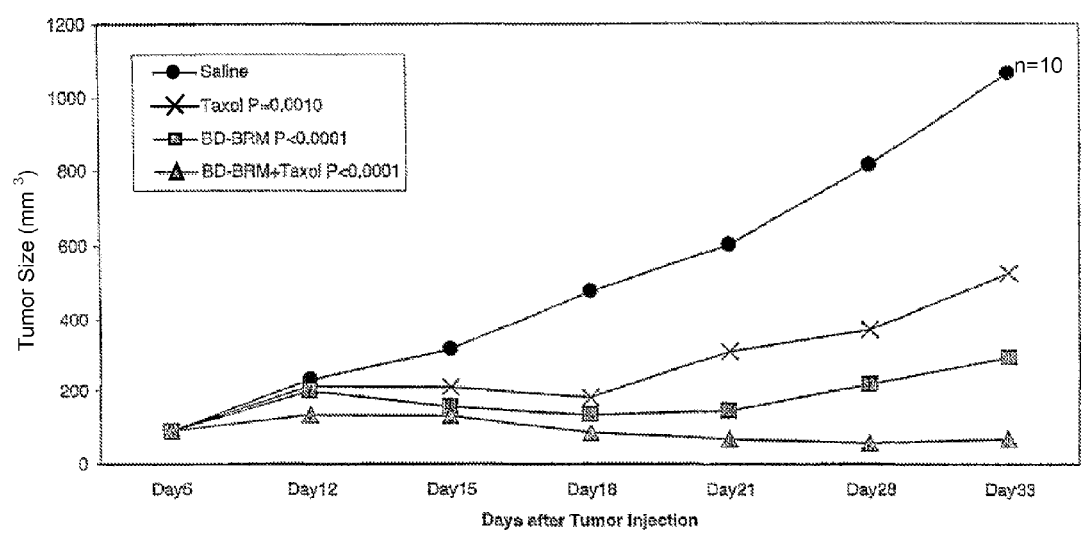
FIG. 10 illustrates the growth of Human Breast Adenocarcinoma (MDA-MB-231) in CD-1 Nude Mice.
Figure 11:
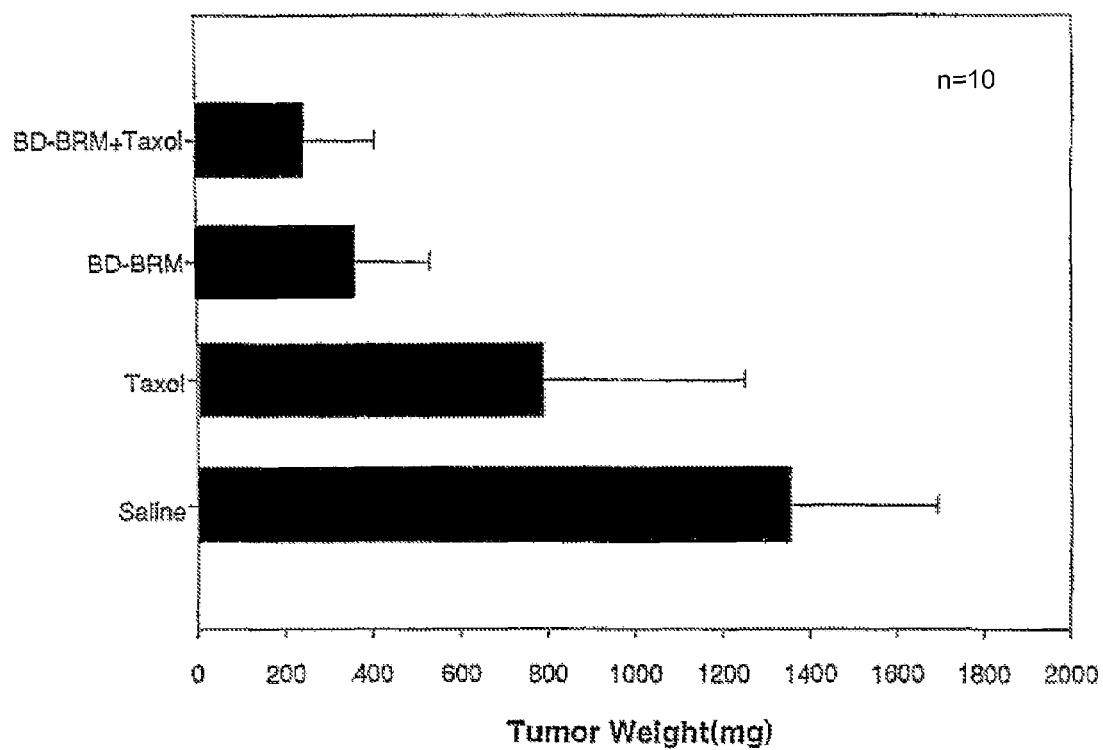
FIG. 11 illustrates the weight of Human Breast Adenocarcinoma (MDA-MB-231) in CD-1 Nude Mice.
Figure 12:
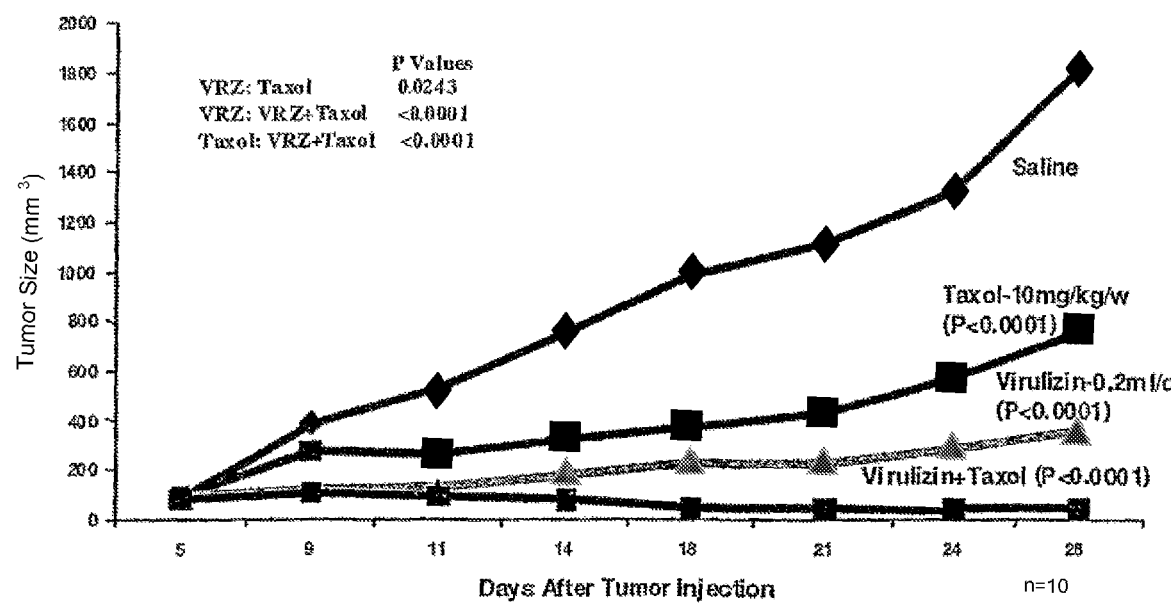
FIG. 12 illustrates the growth of Human Breast Adenocarcinoma (MDA-MB-231) in CD-1 Nude Mice.
Figure 13:
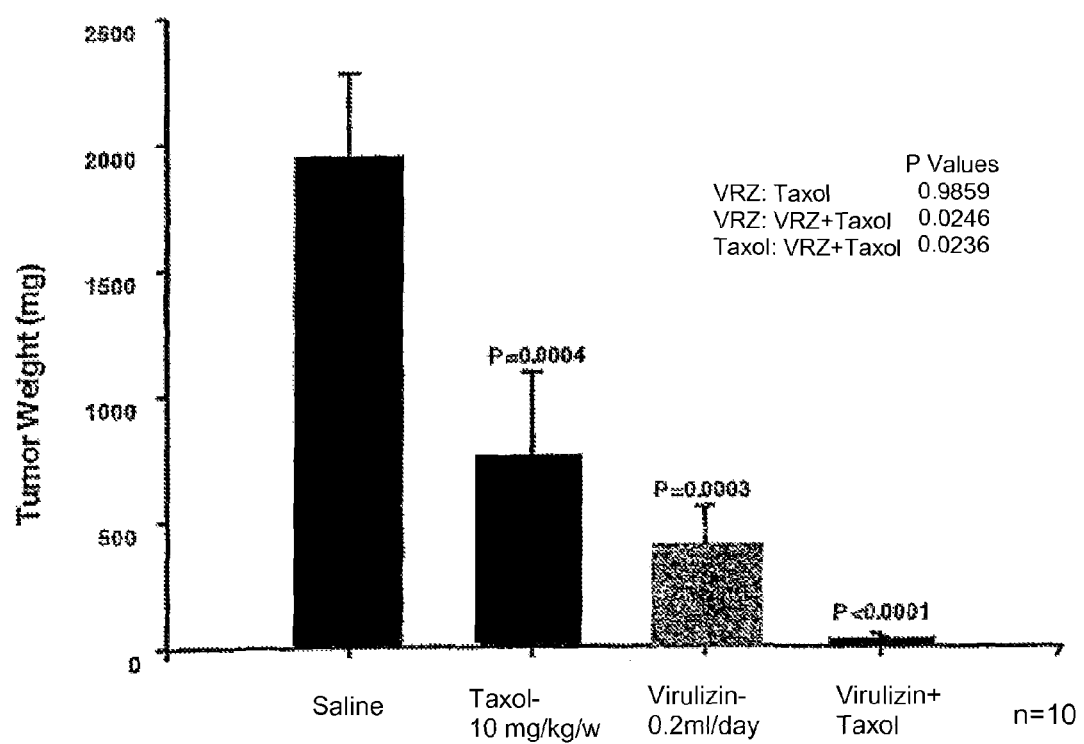
FIG. 13 illustrates the weight of Human Breast Adenocarcinoma (MDA-MB-231) in CD-1 Nude Mice.
Figure 14:
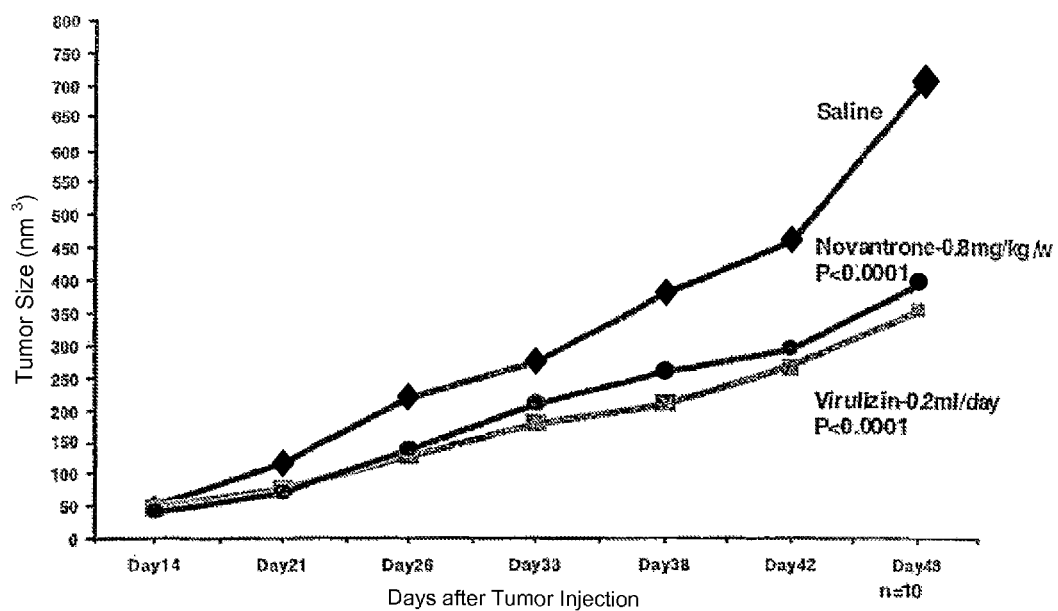
FIG. 14 illustrates the growth of Human Prostate Carcinoma (PC-3) in SCID Mice.
Figure 15:
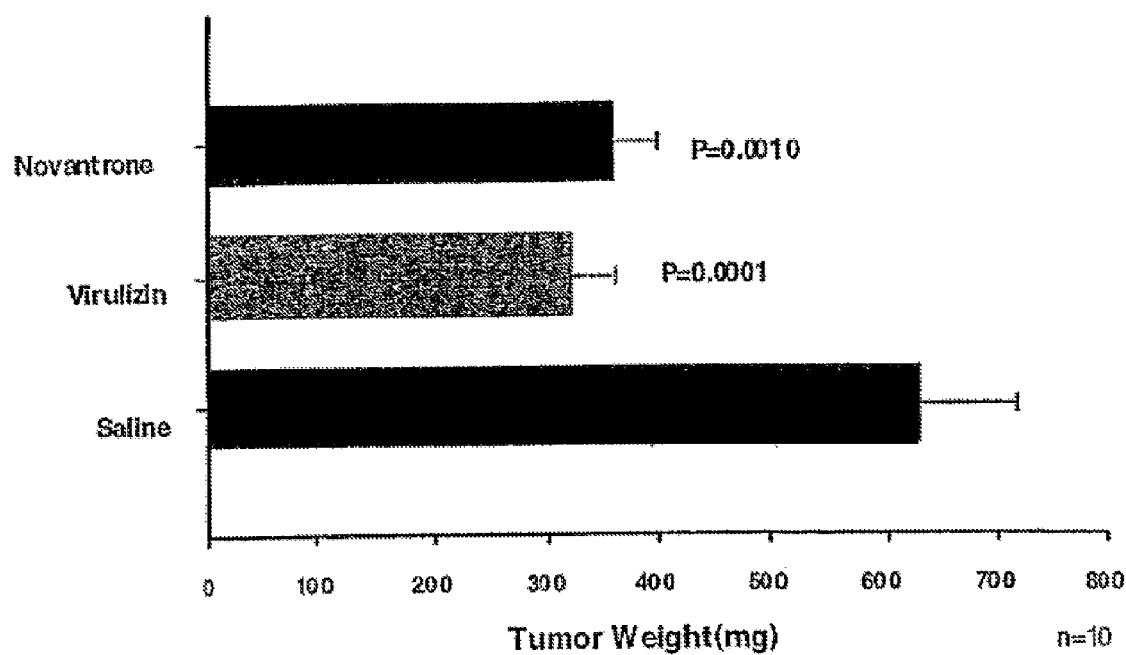
FIG. 15 illustrates the weight of Human Prostate Carcinoma (PC-3) in SCID Mice.
Figure 16:
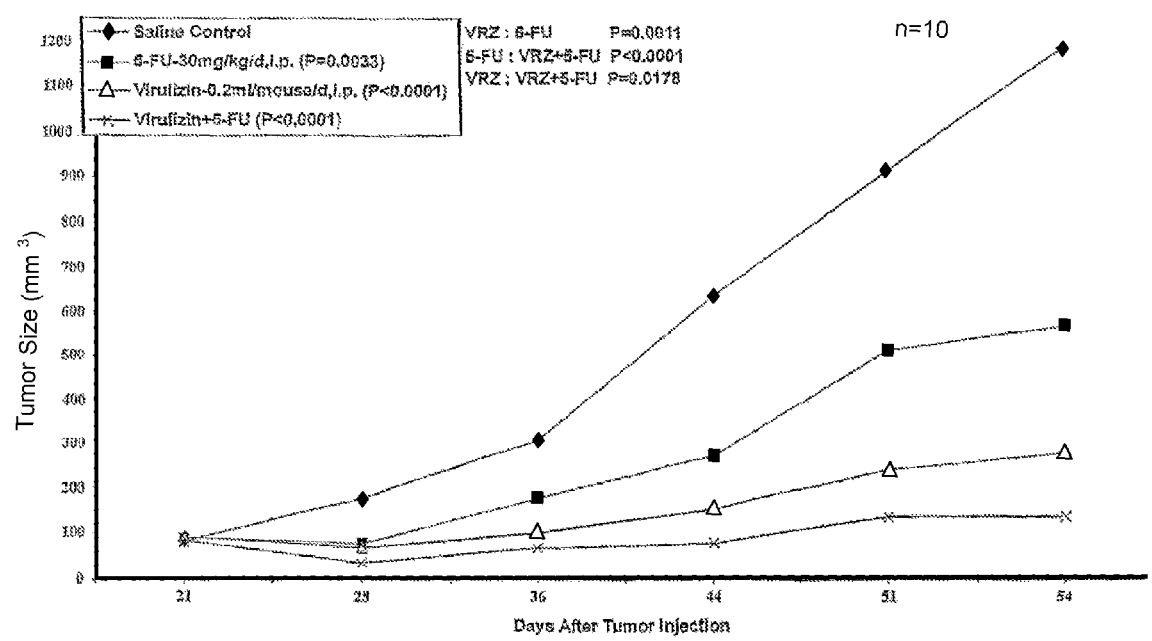
FIG. 16 illustrates the growth of Human Pancreatic Carcinoma (BxPC-3) in CD-1 Nude Mice.
Figure 17:
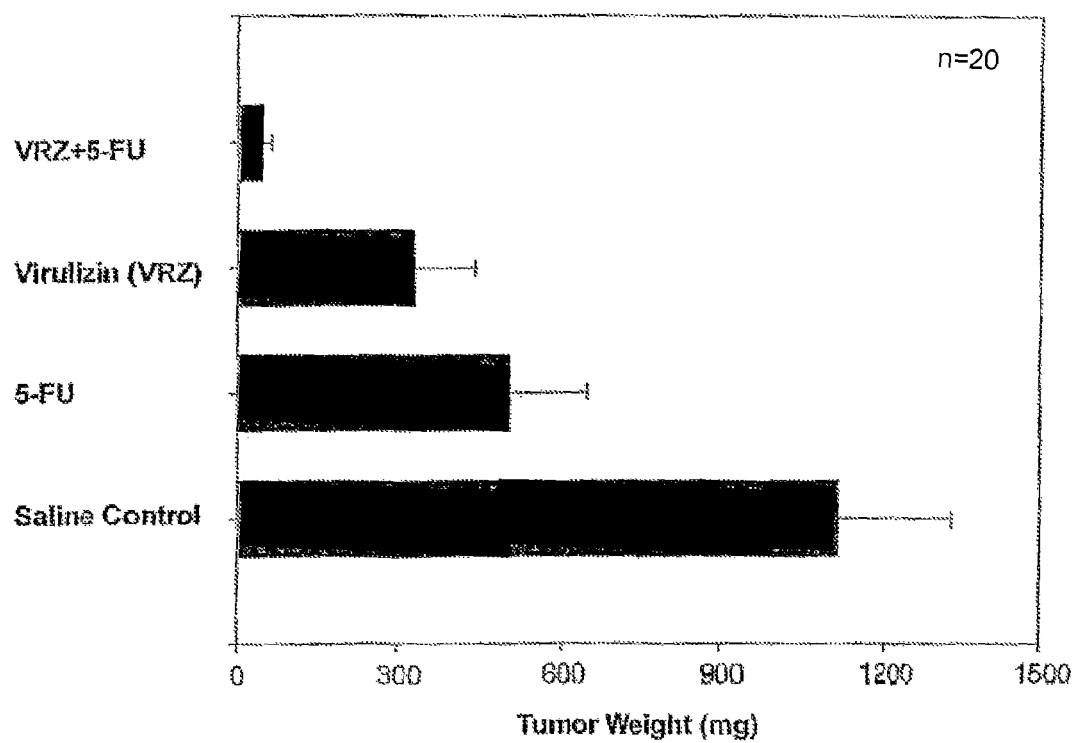
FIG. 17 illustrates the weight of Human Pancreatic Carcinoma (SU.86.86) in CD-1 Nude Mice.
Figure 18:
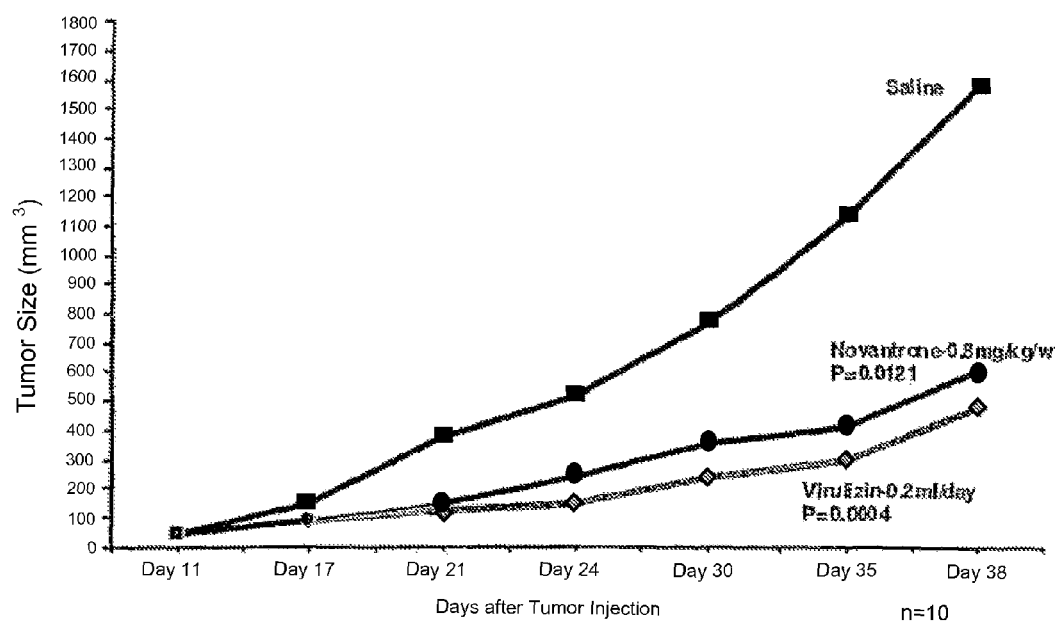
FIG. 18 illustrates the growth of Human Prostate Carcinoma (DU145) in SCID Mice.
Figure 19:
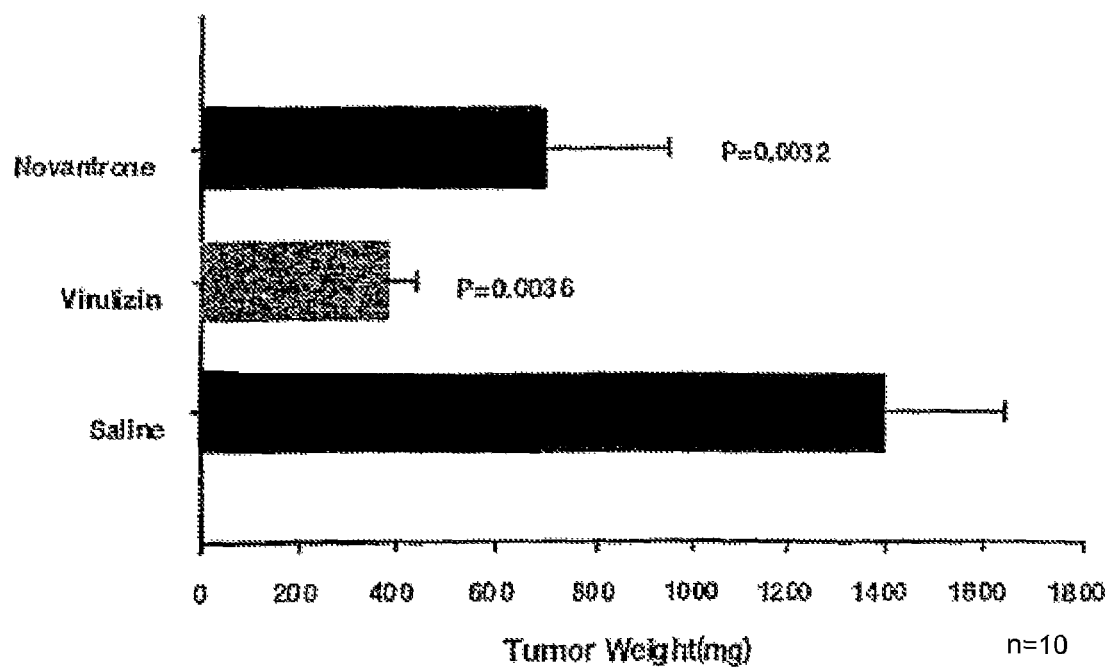
FIG. 19 illustrates the weight of Human Prostate Carcinoma (DU145) in SCID Mice.
Figure 20:
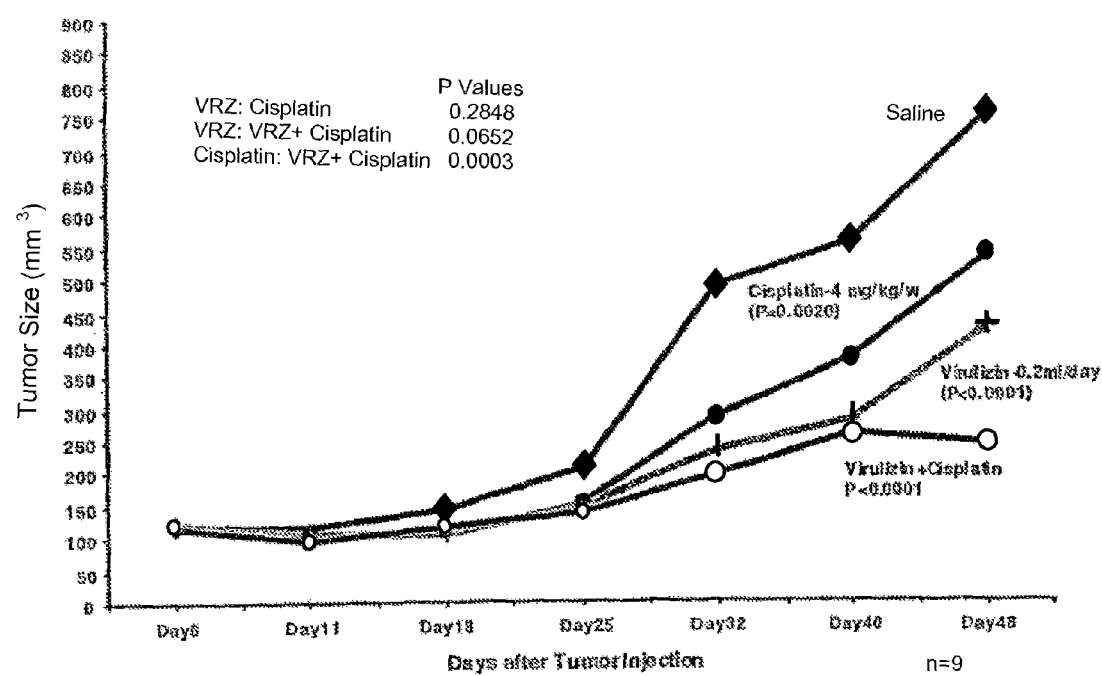
FIG. 20 illustrates the growth of Human Ovary Adenocarcinoma (SK-OV-3) in CD-1 Nude Mice.
Figure 21:
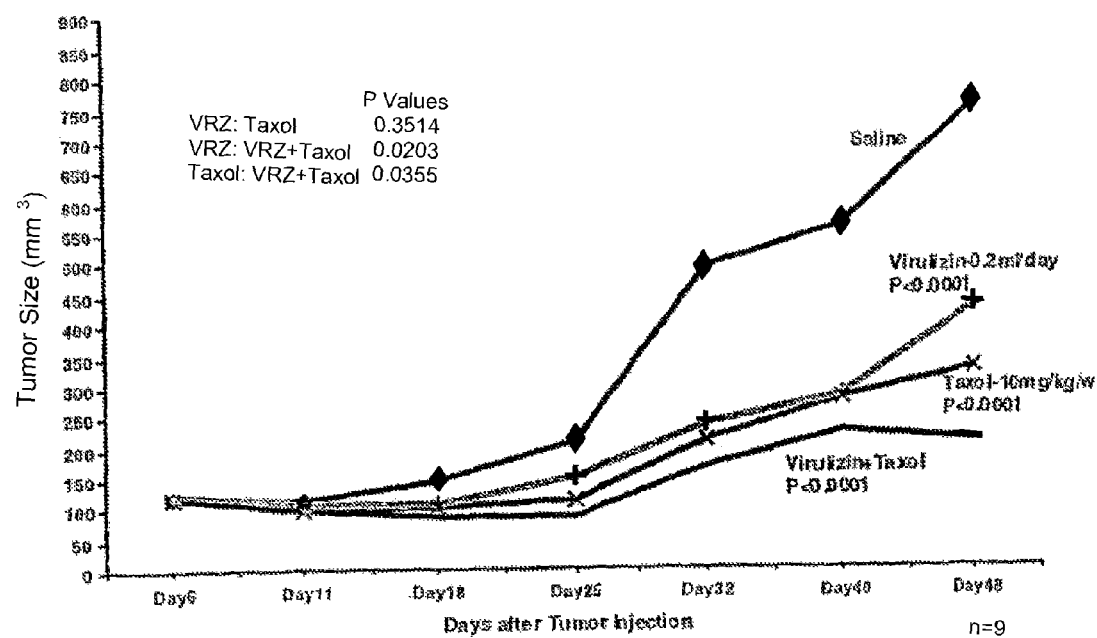
FIG. 21 illustrates the growth of Human Ovary Adenocarcinoma (SK-OV-3) in CD-1 Nude Mice.
Figure 22:
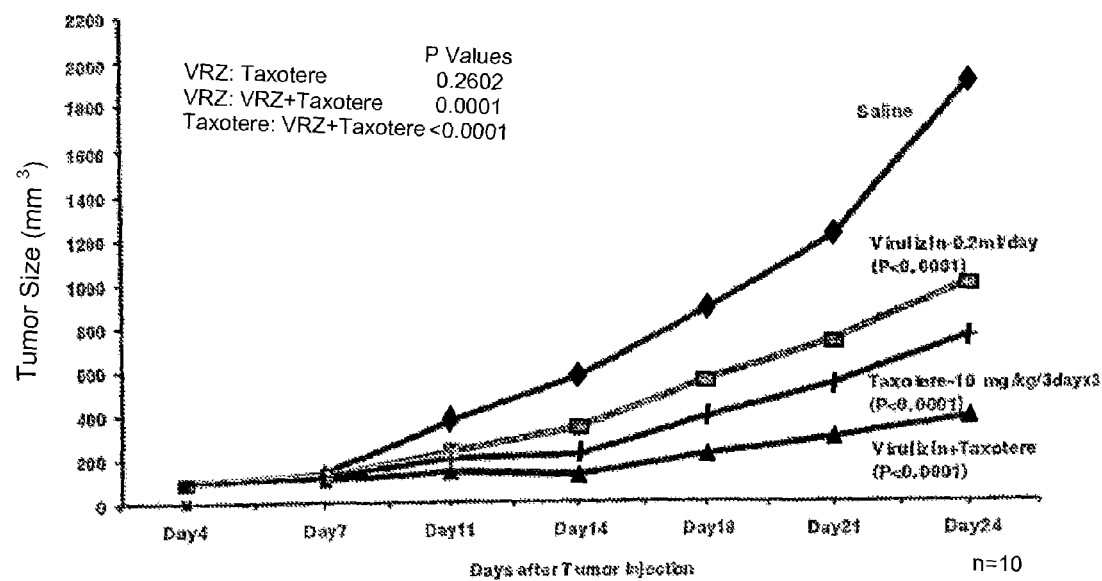
FIG. 22 illustrates the growth of Human Lung Adenocarcinoma (H460) in CD-1 Nude Mice.
Figure 23:
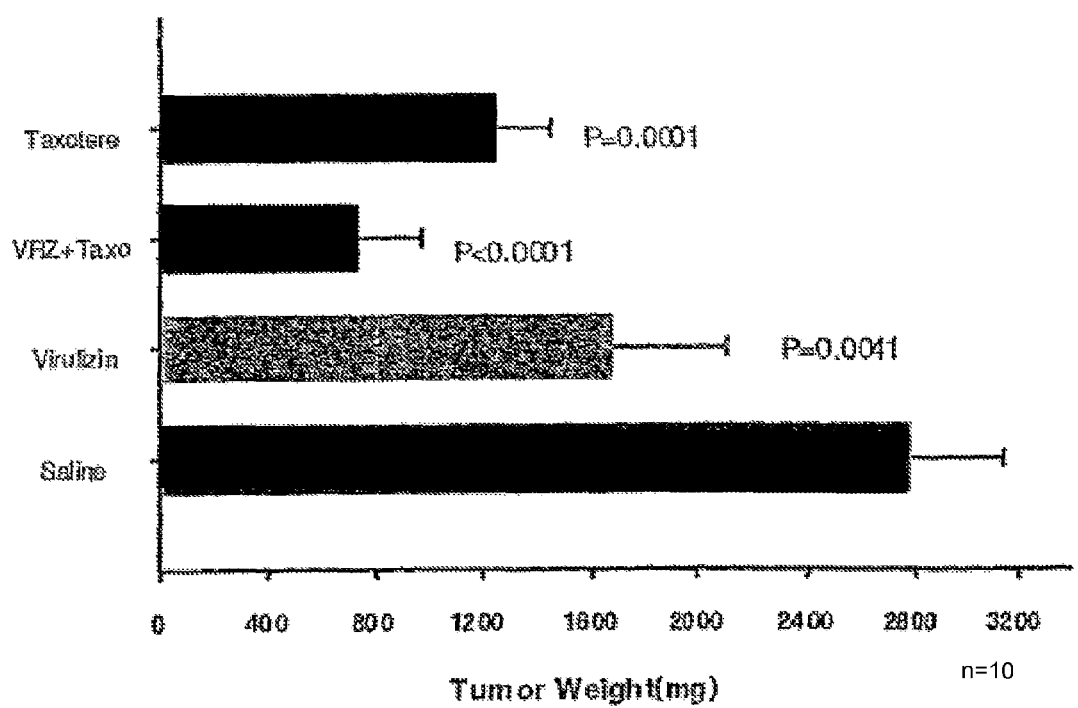
FIG. 23 illustrates the weight of Human Lung Adenocarcinoma (H460) in CD-1 Nude Mice.
Figure 24:
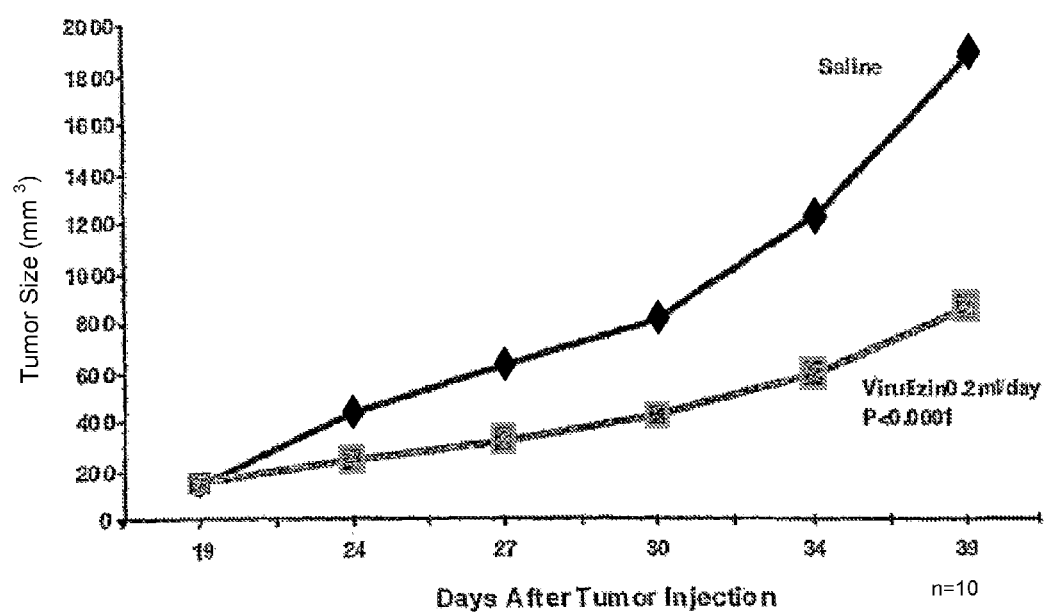
FIG. 24 illustrates the growth of Human Small Cell Lung Carcinoma (H209) in SCID Mice.
Figure 25:
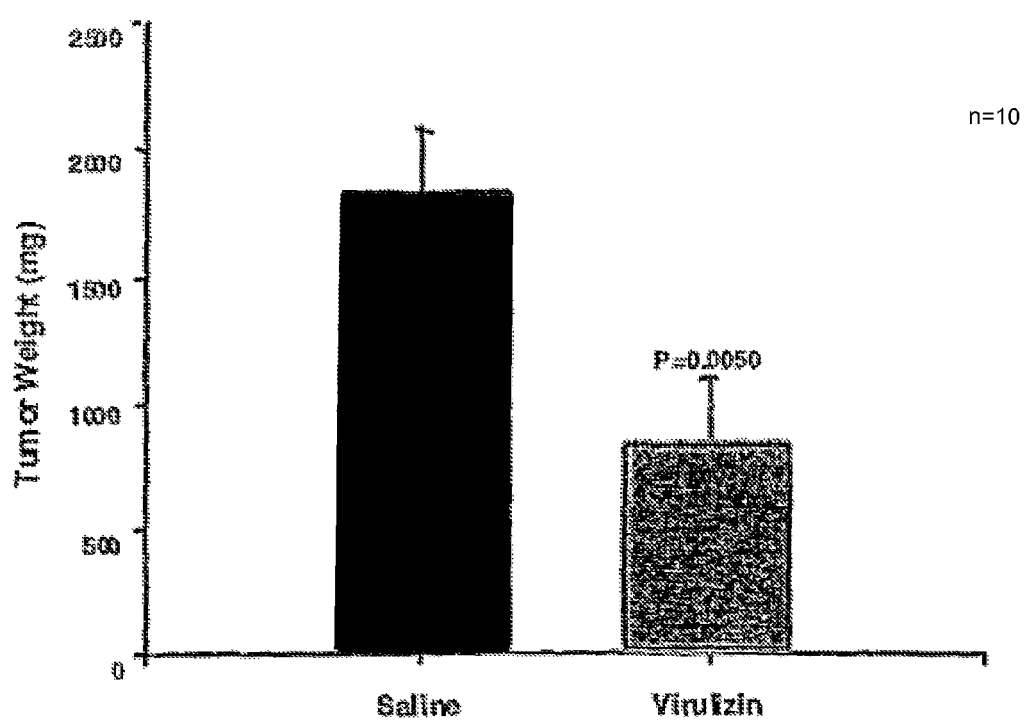
FIG. 25 illustrates the weight of Human Small Cell Lung Carcinoma (H209) in SCID Mice.

The results of the mouse xenograft experiments outlined in the table above are shown in FIGS. 2-25. BD-BRM treatments always resulted in significant delay of tumor growth compared to saline control. Where a chemotherapeutic drug treatment group was included, the delay in tumor growth achieved with BD-BRM was typically superior to the inhibitory effects observed with the chemotherapeutic drug. As indicated in the above table, total regression of the tumor was also observed in some of the animals, when the animals were treated with a BRM composition alone or with a combination of the BD-BRM composition and a chemotherapeutic drug was used. In the remaining animals treated with a combination, significantly enhanced antitumor effects were observed.

The efficacy of the combinations of the invention can also be determined experimentally using other protocols to study animal models grafted with cancerous cells. The animals subjected to the experiment, can be grafted with a tumor fragment, and the graft may be placed subcutaneously. In the case of the treatment of advanced tumors, tumors are allowed to develop to the desired size, animals having insufficiently developed tumors being eliminated. Animals not bearing tumors may also be subjected to the same treatments as the tumor-bearing animals in order to be able to dissociate the toxic effect from the specific effect on the tumor. Treatment

I claim:
1. A composition comprising a combination of:
  (a) a bile-derived composition comprising small molecular weight components of less than 3000 daltons, and having the following properties:
    (i) is extracted from bile of animals;
    (ii) is capable of stimulating monocytes and/or macrophages;
    (iii) is capable of modulating tumor necrosis factor production and/or release;
    (iv) contains no measurable level of IL-1α, IL-1β, TNF, IL-6, IL-8, IL-4, GM-CSF or IFN-gamma;
    (v) is not cytotoxic to human peripheral blood mononuclear cells; and
    (vi) is not an endotoxin; and
  (b) at least one chemotherapeutic drug, wherein said composition has an improved efficacy in the treatment of cancer over treatment with the bile-derived composition alone and over treatment with the at least one chemotherapeutic drug alone, or wherein said composition improves the therapeutic index in the treatment of cancer over the bile-derived composition or the at least one chemotherapeutic drug alone, wherein the cancer is selected from the group consisting of melanoma, breast cancer, ovarian cancer and lung cancer;

wherein when the cancer is melanoma, the at least one chemotherapeutic drug is dacarbazine;
wherein when the cancer is breast cancer, the at least one chemotherapeutic drug is paclitaxel (Taxol);
wherein when the cancer is ovarian cancer, the at least one chemotherapeutic drug is cisplatin or paclitaxel (Taxol); and
wherein when the cancer is lung cancer, the at least one chemotherapeutic drug is docetaxel (Taxotere).

2. The composition according to claim 1, wherein said bile-derived composition and said at least one chemotherapeutic drug are formulated in the same dosage unit, or said bile-derived composition is formulated in a dosage unit and said at least one chemotherapeutic drug is formulated in one or more other dosage units, such that the dosage unit comprising the bile-derived composition and the one or more other dosage units comprising the at least one chemotherapeutic drug are formulated for administration at the same time or at different times.

3. The composition according to claim 1, wherein said bile-derived composition is formulated for intramuscular injection.

4. A pharmaceutical kit comprising:
(a) a dosage unit of a bile-derived composition and a pharmaceutically acceptable carrier wherein the bile-derived composition comprises small molecular weight components of less than 3000 daltons, and has the following properties:
  (i) is extracted from bile of animals;
  (ii) is capable of stimulating monocytes and/or macrophages;
  (iii) is capable of modulating tumor necrosis factor production and/or release;
  (iv) contains no measurable level of IL-1α, IL-1β, TNF, IL-6, IL-8, IL-4, GM-CSF or IFN-gamma;
  (v) is not cytotoxic to human peripheral blood mononuclear cells; and
  (vi) is not an endotoxin; and
(b) a dosage unit of at least one chemotherapeutic drug and a pharmaceutically acceptable carrier, said (a) and (b) being provided in amounts that provide an improved efficacy in the treatment of cancer over treatment with the bile-derived composition alone and over treatment with the at least one chemotherapeutic drug alone or that improve the therapeutic index in the treatment of cancer over the bile-derived composition or the at least one chemotherapeutic drug alone, wherein the cancer is selected from the group consisting of melanoma, breast cancer, ovarian cancer and lung cancer;
wherein when the cancer is melanoma, the at least one chemotherapeutic drug is dacarbazine;
wherein when the cancer is breast cancer, the at least one chemotherapeutic drug is paclitaxel (Taxol);
wherein when the cancer is ovarian cancer, the at least one chemotherapeutic drug is cisplatin or paclitaxel (Taxol); and
wherein when the cancer is lung cancer, the at least one chemotherapeutic drug is docetaxel (Taxotere).

5. The pharmaceutical kit according to claim 4, wherein said bile-derived composition is formulated for intramuscular injection.

6. A pharmaceutical composition comprising the composition according to claim 2, wherein said same dosage unit, said dosage unit or said one or more other dosage units further comprise a pharmaceutically acceptable carrier; wherein said pharmaceutical composition has an improved efficacy in the treatment of cancer over treatment with the bile-derived composition alone and over treatment with the at least one chemotherapeutic drug alone or wherein said pharmaceutical composition has an improved therapeutic index in the treatment of cancer over the bile-derived composition or the at least one chemotherapeutic drug alone, wherein the cancer is selected from the group consisting of melanoma, breast cancer, ovarian cancer and lung cancer;
wherein when the cancer is melanoma, the at least one chemotherapeutic drug is dacarbazine;
wherein when the cancer is breast cancer, the at least one chemotherapeutic drug is paclitaxel (Taxol);
wherein when the cancer is ovarian cancer, the at least one chemotherapeutic drug is cisplatin or paclitaxel (Taxol); and
wherein when the cancer is lung cancer, the at least one chemotherapeutic drug is docetaxel (Taxotere).

7. A method for treating cancer comprising:
(a) administering a therapeutically effective amount of a bile-derived composition comprising small molecular weight components of less than 3000 daltons to a patient in need thereof, the bile-derived composition having the following properties:
  (i) is extracted from bile of animals;
  (ii) is capable of stimulating monocytes and/or macrophages;
  (iii) is capable of modulating tumor necrosis factor production and/or release;
  (iv) contains no measurable level of IL-1α, IL-1β, TNF, IL-6, IL-8, IL-4, GM-CSF or IFN-gamma;
  (v) is not cytotoxic to human peripheral blood mononuclear cells; and
  (vi) is not an endotoxin; and
(b) administering a therapeutically effective amount of at least one chemotherapeutic drug to the patient in need thereof,
wherein said method results in an improved efficacy in the treatment of cancer over administering the bile-derived composition alone and over administering the at least one chemotherapeutic drug alone or improves the therapeutic index in the treatment of cancer over administering the bile-derived composition or administering the at least one chemotherapeutic drug alone, wherein the cancer is selected from the group consisting of melanoma, breast cancer, ovarian cancer and lung cancer;
wherein when the cancer is melanoma, the at least one chemotherapeutic drug is dacarbazine;
wherein when the cancer is breast cancer the at least one chemotherapeutic drug is paclitaxel (Taxol);
wherein when the cancer is ovarian cancer, the at least one chemotherapeutic drug is cisplatin or paclitaxel (Taxol); and
wherein when the cancer is lung cancer, the at least one chemotherapeutic drug is docetaxel (Taxotere).

8. The method according to claim 7, wherein administration of said bile-derived composition is via intramuscular injection.

9. The method according to claim 7, wherein said bile-derived composition and said at least one chemotherapeutic drug are formulated in the same dosage unit for administration, or said bile-derived composition is formulated in a dosage unit and said at least one chemotherapeutic drug is formulated in one or more other dosage units, such that the dosage unit comprising the bile-derived composition and the one or more other dosage units comprising the at least one chemotherapeutic drug are formulated for administration at the same time or at different times.

* * * * *

UNITED STATES PATENT AND TRADEMARK OFFICE
CERTIFICATE OF CORRECTION

PATENT NO. : 8,394,418 B2
APPLICATION NO. : 13/008304
DATED : March 12, 2013
INVENTOR(S) : Aiping Young It is certified that error appears in the above-identified patent and that said Letters Patent is hereby corrected as shown below:

In the Specification

Column 6,
Line 45, "11-2;" should read --Il-2;--.

Column 12,
Line 4, "homoblastic leukemia" should read --hemoblastic leukemia--.

Signed and Sealed this
Thirtieth Day of July, 2013

Teresa Stanek Rea
*Acting Director of the United States Patent and Trademark Office*